US011266344B2

(12) United States Patent
Kim et al.

(10) Patent No.: US 11,266,344 B2
(45) Date of Patent: Mar. 8, 2022

(54) METHOD FOR MEASURING SKIN CONDITION AND ELECTRONIC DEVICE THEREFOR

(71) Applicant: Samsung Electronics Co., Ltd., Suwon-si (KR)

(72) Inventors: Young-hyun Kim, Suwon-si (KR); Jeong-gun Lee, Seoul (KR); Shin-hee Cho, Suwon-si (KR); Moo-rim Kim, Suwon-si (KR); Jin-kyeong Kim, Yongin-si (KR); Min-sun Park, Seoul (KR); Seung-jun Lee, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 440 days.

(21) Appl. No.: 16/335,470

(22) PCT Filed: Aug. 18, 2017

(86) PCT No.: PCT/KR2017/009012
§ 371 (c)(1),
(2) Date: Mar. 21, 2019

(87) PCT Pub. No.: WO2018/056584
PCT Pub. Date: Mar. 29, 2018

(65) Prior Publication Data
US 2021/0282703 A1    Sep. 16, 2021

Related U.S. Application Data

(60) Provisional application No. 62/397,505, filed on Sep. 21, 2016.

(30) Foreign Application Priority Data

Oct. 28, 2016  (KR) .......................... 10-2016-0142110
Dec. 7, 2016   (KR) .......................... 10-2016-0165891

(51) Int. Cl.
*A61B 5/00*    (2006.01)

(52) U.S. Cl.
CPC ............ *A61B 5/443* (2013.01); *A61B 5/0059* (2013.01); *A61B 5/6833* (2013.01); *A61B 5/742* (2013.01); *A61B 5/685* (2013.01)

(58) Field of Classification Search
CPC ..... A61B 5/6833; A61B 5/443; A61B 5/4848; A61B 55/443; A61B 5/0059;
(Continued)

(56) References Cited

U.S. PATENT DOCUMENTS 6,419,935 B1 * 7/2002 Gueret ................ A61K 8/0208
                                                424/401
7,393,195 B2   7/2008 Keller et al.
(Continued)

FOREIGN PATENT DOCUMENTS

CN    102065750 A    5/2011
CN    103860169 A    6/2014
(Continued)

OTHER PUBLICATIONS

Machine Translation of JP 2011-200465 from Global Dossier (Year: 2021).*
(Continued)

*Primary Examiner* — Eric F Winakur
*Assistant Examiner* — Alice Ling Zou
(74) *Attorney, Agent, or Firm* — Jefferson IP Law, LLP

(57) ABSTRACT

A method for measuring skin by an electronic device is provided. The method for measuring skin by the electronic device includes an operation of irradiating at least one light into skin to which a patch is adhered, an operation of detecting at least one reflected light on the basis of an amount of moisture in the skin, which is changed by physiologically active substances injected through the patch,
(Continued)

corresponding to the irradiated light, an operation of generating patch adherence information indicating a skin adhesive state of the patch on the basis of the detection result of the at least one reflected light and an operation of providing the generated patch adherence information to an output unit or a communication unit.

10 Claims, 30 Drawing Sheets

(58) Field of Classification Search
CPC ... A61B 5/0075; A61B 5/0537; A61B 5/1455; A61B 5/441; A61B 5/4875; A61B 5/685; A61B 5/742; A61B 2562/029; A61Q 19/00; A61Q 19/007; A61Q 90/00; A61P 17/00; A61P 17/16
See application file for complete search history.

(56) References Cited

U.S. PATENT DOCUMENTS

| | | | |
|---|---|---|---|
| 7,808,064 B2 | 10/2010 | Kawasaki et al. | |
| 7,859,277 B2 | 12/2010 | Mayder et al. | |
| 8,280,469 B2 * | 10/2012 | Baker, Jr. | A61B 5/14551 600/310 |
| 8,309,040 B2 | 11/2012 | Chung et al. | |
| 8,471,279 B2 | 6/2013 | Park et al. | |
| 8,489,177 B2 | 7/2013 | Welch | |
| 8,574,943 B2 | 11/2013 | Murray et al. | |
| 8,603,414 B2 | 12/2013 | Omuro et al. | |
| 8,613,845 B2 | 12/2013 | Maxwell et al. | |
| 8,753,959 B2 | 6/2014 | Yun et al. | |
| 8,821,214 B2 | 9/2014 | Joseph | |
| 8,890,075 B2 | 11/2014 | Gamel et al. | |
| 8,900,194 B2 | 12/2014 | Clarke et al. | |
| 8,927,258 B2 | 1/2015 | Galiano et al. | |
| 9,022,997 B2 | 5/2015 | Chung et al. | |
| 9,068,544 B2 | 6/2015 | Stucchi et al. | |
| 9,076,626 B2 | 7/2015 | Ribton et al. | |
| 9,082,840 B2 | 7/2015 | Yun et al. | |
| 9,085,835 B2 | 7/2015 | Tang | |
| 9,089,863 B2 | 7/2015 | Crouch et al. | |
| 9,115,755 B2 | 8/2015 | Kolev et al. | |
| 9,198,955 B2 | 12/2015 | Deykin | |
| 9,206,758 B2 | 12/2015 | Rodriguez-Amaya et al. | |
| 9,234,853 B2 | 1/2016 | Beijert | |
| 9,309,415 B2 | 4/2016 | Baumgart et al. | |
| 9,315,564 B2 | 4/2016 | Serraima et al. | |
| 9,381,680 B2 | 7/2016 | Oh et al. | |
| 9,382,643 B2 | 7/2016 | Moore et al. | |
| 9,422,653 B2 | 8/2016 | Wu et al. | |
| 9,427,679 B2 | 8/2016 | Mahmoudi et al. | |
| 9,475,034 B2 | 10/2016 | Vincent et al. | |
| 9,504,825 B2 | 11/2016 | Ajiki et al. | |
| 9,512,543 B2 | 12/2016 | Turner et al. | |
| 9,566,423 B2 | 2/2017 | Ueno et al. | |
| 9,580,848 B2 | 2/2017 | Henderson et al. | |
| 9,605,338 B2 | 3/2017 | Ramm et al. | |
| 9,636,490 B2 | 5/2017 | Masaoka et al. | |
| 9,657,341 B2 | 5/2017 | Park et al. | |
| 9,675,790 B2 | 6/2017 | Stoeber et al. | |
| 9,757,487 B2 | 9/2017 | Roy et al. | |
| 9,775,799 B2 | 10/2017 | Sugahara et al. | |
| 9,821,114 B2 | 11/2017 | Cabrera Aquino et al. | |
| 9,849,170 B2 | 12/2017 | Machida et al. | |
| 9,849,272 B2 | 12/2017 | Yamamoto et al. | |
| 9,862,799 B2 | 1/2018 | Chen et al. | |
| 9,889,285 B2 | 2/2018 | Sumida et al. | |
| 9,913,970 B2 | 3/2018 | Arami et al. | |
| 9,974,935 B2 | 5/2018 | Toyohara et al. | |
| 9,975,064 B2 | 5/2018 | Mahmoudi et al. | |
| 9,993,815 B2 | 6/2018 | Immerzeel et al. | |
| 9,994,686 B2 | 6/2018 | Wong et al. | |
| 10,039,911 B2 | 8/2018 | Yamamoto et al. | |
| 10,046,152 B2 | 8/2018 | Sumida et al. | |
| 10,059,079 B2 | 8/2018 | Kunal et al. | |
| 10,105,317 B2 | 10/2018 | Yu et al. | |
| 10,111,782 B2 | 10/2018 | Fitz et al. | |
| 10,183,156 B2 | 1/2019 | Ross et al. | |
| 2004/0009141 A1 | 1/2004 | Koenig et al. | |
| 2005/0004508 A1 | 1/2005 | Sun et al. | |
| 2010/0191177 A1 | 7/2010 | Chang et al. | |
| 2010/0216373 A1 | 8/2010 | Borucki et al. | |
| 2010/0243154 A1 | 9/2010 | Wiessner et al. | |
| 2011/0077527 A1 | 3/2011 | Yang et al. | |
| 2011/0127690 A1 | 6/2011 | Honda et al. | |
| 2011/0152792 A1 | 6/2011 | Takada | |
| 2011/0183583 A1 | 7/2011 | Joseph | |
| 2011/0184257 A1 | 7/2011 | Boll et al. | |
| 2011/0192562 A1 | 8/2011 | Motoi et al. | |
| 2011/0213335 A1 | 9/2011 | Burton et al. | |
| 2011/0230739 A1 | 9/2011 | Gretz et al. | |
| 2011/0275973 A1 | 11/2011 | Rizvi et al. | |
| 2011/0288485 A1 | 11/2011 | Tokumoto et al. | |
| 2012/0004626 A1 | 1/2012 | Kuwahara et al. | |
| 2012/0091699 A1 | 4/2012 | Krueger et al. | |
| 2013/0037481 A1 | 2/2013 | Lalouch et al. | |
| 2013/0041330 A1 | 2/2013 | Matsudo et al. | |
| 2013/0072902 A1 | 3/2013 | Takada et al. | |
| 2013/0304163 A1 | 11/2013 | Moon et al. | |
| 2013/0345671 A1 | 12/2013 | Ryu et al. | |
| 2014/0236090 A1 | 8/2014 | Colburn et al. | |
| 2014/0259484 A1 | 9/2014 | Baer et al. | |
| 2014/0309508 A1 | 10/2014 | Kim et al. | |
| 2014/0350395 A1 | 11/2014 | Shachaf et al. | |
| 2015/0028195 A1 | 1/2015 | King et al. | |
| 2015/0057604 A1 | 2/2015 | Arami et al. | |
| 2015/0112250 A1 | 4/2015 | Kwon | |
| 2015/0112269 A1 | 4/2015 | Sumida et al. | |
| 2015/0115071 A1 | 4/2015 | Go et al. | |
| 2015/0182737 A1 | 7/2015 | Ajiki et al. | |
| 2015/0216796 A1 | 8/2015 | Ishibashi et al. | |
| 2015/0223749 A1 | 8/2015 | Park et al. | |
| 2015/0275421 A1 | 10/2015 | Cardinali et al. | |
| 2015/0351690 A1 | 12/2015 | Toth et al. | |
| 2015/0353726 A1 | 12/2015 | Wong et al. | |
| 2016/0095592 A1 | 4/2016 | Levinson et al. | |
| 2016/0120588 A1 | 5/2016 | Amoah et al. | |
| 2016/0129164 A1 | 5/2016 | Lee et al. | |
| 2016/0129279 A1 | 5/2016 | Ferolito | |
| 2016/0199664 A1 | 7/2016 | Hogset et al. | |
| 2016/0206866 A1 | 7/2016 | Yamamoto et al. | |
| 2016/0354590 A1 | 12/2016 | Lee | |
| 2017/0073515 A1 | 3/2017 | Wong et al. | |
| 2017/0080196 A1 | 3/2017 | Lee et al. | |
| 2017/0120024 A1 | 5/2017 | Lee | |
| 2017/0189661 A1 | 7/2017 | Lee | |
| 2019/0015652 A1 | 1/2019 | Kominami et al. | |

FOREIGN PATENT DOCUMENTS

| | | | |
|---|---|---|---|
| EP | 2 371 285 A1 | | 10/2011 |
| EP | 2 789 276 B1 | | 9/2015 |
| JP | 2008188302 A | * | 8/2008 |
| JP | 2009-028275 A | | 2/2009 |
| JP | 2011-200465 A | | 10/2011 |
| JP | 2015-142718 A | | 8/2015 |
| KR | 20080014461 A | * | 2/2008 |
| KR | 10-2010-0056552 A | | 5/2010 |
| KR | 10-2010-0064669 A | | 6/2010 |
| KR | 10-0972800 B1 | | 7/2010 |
| KR | 10-0973404 B1 | | 7/2010 |
| KR | 10-2010-0090773 A | | 8/2010 |
| KR | 10-2010-0091199 A | | 8/2010 |
| KR | 10-0974985 B1 | | 8/2010 |
| KR | 10-2010-0096999 A | | 9/2010 |
| KR | 10-0984682 B1 | | 10/2010 |
| KR | 10-2011-0005767 A | | 1/2011 |
| KR | 10-1006546 B1 | | 1/2011 |
| KR | 10-2011-0012978 A | | 2/2011 |
| KR | 10-2011-0018358 A | | 2/2011 |
| KR | 10-2011-0019442 A | | 2/2011 |
| KR | 10-1017392 B1 | | 2/2011 |

(56) References Cited

FOREIGN PATENT DOCUMENTS

| | | |
|---|---|---|
| KR | 10-2011-0021724 A | 3/2011 |
| KR | 10-2011-0033277 A | 3/2011 |
| KR | 10-1028182 B1 | 4/2011 |
| KR | 10-1030752 B1 | 4/2011 |
| KR | 10-1031030 B1 | 4/2011 |
| KR | 10-2011-0046205 A | 5/2011 |
| KR | 10-1032298 B1 | 5/2011 |
| KR | 10-1033078 B1 | 5/2011 |
| KR | 10-2011-0067008 A | 6/2011 |
| KR | 10-2011-0067009 A | 6/2011 |
| KR | 10-1041431 B1 | 6/2011 |
| KR | 10-1047460 B1 | 7/2011 |
| KR | 10-2011-0086854 A | 8/2011 |
| KR | 10-1054732 B1 | 8/2011 |
| KR | 10-2011-0102871 A | 9/2011 |
| KR | 10-2011-0107333 A | 9/2011 |
| KR | 10-2011-0113797 A | 10/2011 |
| KR | 10-2011-0118627 A | 10/2011 |
| KR | 10-1071658 B1 | 10/2011 |
| KR | 10-2010-0118815 A | 11/2011 |
| KR | 10-2011-0120900 A | 11/2011 |
| KR | 10-1080034 B1 | 11/2011 |
| KR | 10-2011-0131228 A | 12/2011 |
| KR | 10-2012-0007515 A | 1/2012 |
| KR | 10-1103088 B1 | 1/2012 |
| KR | 10-1103558 B1 | 1/2012 |
| KR | 10-1103620 B1 | 1/2012 |
| KR | 10-1105724 B1 | 1/2012 |
| KR | 10-1108992 B1 | 1/2012 |
| KR | 10-2012-0012093 A | 2/2012 |
| KR | 10-2012-0013337 A | 2/2012 |
| KR | 10-2012-0016190 A | 2/2012 |
| KR | 10-1112095 B1 | 2/2012 |
| KR | 10-1128341 B1 | 3/2012 |
| KR | 10-1129887 B1 | 3/2012 |
| KR | 10-2012-0058371 A | 6/2012 |
| KR | 10-2012-0059495 A | 6/2012 |
| KR | 10-1149761 B1 | 6/2012 |
| KR | 10-1159134 B1 | 6/2012 |
| KR | 10-2012-0076348 A | 7/2012 |
| KR | 10-2012-0082880 A | 7/2012 |
| KR | 10-2012-0087197 A | 8/2012 |
| KR | 10-2012-0087588 A | 8/2012 |
| KR | 10-2012-0089276 A | 8/2012 |
| KR | 10-1171888 B1 | 8/2012 |
| KR | 10-1175326 B1 | 8/2012 |
| KR | 10-2012-0099101 A | 9/2012 |
| KR | 10-1180277 B1 | 9/2012 |
| KR | 10-1180775 B1 | 9/2012 |
| KR | 10-1180776 B1 | 9/2012 |
| KR | 10-2012-0129779 A | 11/2012 |
| KR | 10-2012-0138235 A | 12/2012 |
| KR | 10-1207561 B1 | 12/2012 |
| KR | 10-1219569 B1 | 1/2013 |
| KR | 10-1224629 B1 | 1/2013 |
| KR | 10-1241059 B1 | 3/2013 |
| KR | 10-2013-0040783 A | 4/2013 |
| KR | 10-2013-0043298 A | 4/2013 |
| KR | 10-1250263 B1 | 4/2013 |
| KR | 10-2013-0045982 A | 5/2013 |
| KR | 10-2013-0060684 A | 6/2013 |
| KR | 10-2013-0069662 A | 6/2013 |
| KR | 10-2013-0076825 A | 7/2013 |
| KR | 10-2013-0085952 A | 7/2013 |
| KR | 10-1278467 B1 | 7/2013 |
| KR | 10-2013-0093212 A | 8/2013 |
| KR | 10-2013-0094196 A | 8/2013 |
| KR | 10-2013-0094197 A | 8/2013 |
| KR | 10-2013-0094226 A | 8/2013 |
| KR | 10-1295687 B1 | 8/2013 |
| KR | 10-2013-0101109 A | 9/2013 |
| KR | 10-2013-0105599 A | 9/2013 |
| KR | 10-1307335 B1 | 9/2013 |
| KR | 10-2013-0108091 A | 10/2013 |
| KR | 10-1323980 B1 | 10/2013 |
| KR | 10-1324790 B1 | 10/2013 |
| KR | 10-2013-0124484 A | 11/2013 |
| KR | 10-0406450 B1 | 11/2013 |
| KR | 10-1325010 B1 | 11/2013 |
| KR | 10-2013-0138243 A | 12/2013 |
| KR | 10-1342178 B1 | 12/2013 |
| KR | 10-2014-0004723 A | 1/2014 |
| KR | 10-2014-0006167 A | 1/2014 |
| KR | 10-2014-0008428 A | 1/2014 |
| KR | 10-1350626 B1 | 1/2014 |
| KR | 10-2014-0022607 A | 2/2014 |
| KR | 10-2014-0028333 A | 3/2014 |
| KR | 10-2014-0033320 A | 3/2014 |
| KR | 10-2014-0038383 A | 3/2014 |
| KR | 10-1379278 B1 | 3/2014 |
| KR | 10-2014-0044098 A | 4/2014 |
| KR | 10-1383285 B1 | 4/2014 |
| KR | 10-1386319 B1 | 4/2014 |
| KR | 10-2014-0074383 A | 6/2014 |
| KR | 10-1401133 B1 | 6/2014 |
| KR | 10-2014-0083983 A | 7/2014 |
| KR | 10-1423590 B1 | 7/2014 |
| KR | 10-2014-0095342 A | 8/2014 |
| KR | 10-2014-0096151 A | 8/2014 |
| KR | 10-2014-0097454 A | 8/2014 |
| KR | 10-1436000 B1 | 8/2014 |
| KR | 10-2014-0105614 A | 9/2014 |
| KR | 10-2014-0105615 A | 9/2014 |
| KR | 10-2014-0105686 A | 9/2014 |
| KR | 10-2014-0109863 A | 9/2014 |
| KR | 10-2014-0110833 A | 9/2014 |
| KR | 10-2014-0114843 A | 9/2014 |
| KR | 10-2014-0134937 A | 11/2014 |
| KR | 10-1458172 B1 | 11/2014 |
| KR | 10-2014-0143416 A | 12/2014 |
| KR | 10-2014-0146062 A | 12/2014 |
| KR | 10-1471275 B1 | 12/2014 |
| KR | 10-1476923 B1 | 12/2014 |
| KR | 10-1476924 B1 | 12/2014 |
| KR | 10-2015-0003745 A | 1/2015 |
| KR | 10-2015-0010744 A | 1/2015 |
| KR | 10-1484161 B1 | 1/2015 |
| KR | 10-2015-0017738 A | 2/2015 |
| KR | 10-1493327 B1 | 2/2015 |
| KR | 10-2015-0021573 A | 3/2015 |
| KR | 10-2015-0022011 A | 3/2015 |
| KR | 10-2015-0027785 A | 3/2015 |
| KR | 10-1497880 B1 | 3/2015 |
| KR | 10-2015-0037745 A | 4/2015 |
| KR | 10-1508878 B1 | 4/2015 |
| KR | 10-1514560 B1 | 4/2015 |
| KR | 10-2015-0052092 A | 5/2015 |
| KR | 10-2015-0055914 A | 5/2015 |
| KR | 10-2015-0073166 A | 6/2015 |
| KR | 10-1525970 B1 | 6/2015 |
| KR | 10-1531767 B1 | 6/2015 |
| KR | 10-2015-0077258 A | 7/2015 |
| KR | 10-2015-0084866 A | 7/2015 |
| KR | 10-1536287 B1 | 7/2015 |
| KR | 10-1537582 B1 | 7/2015 |
| KR | 10-2015-0094196 A | 8/2015 |
| KR | 10-2015-0098548 A | 8/2015 |
| KR | 10-1542549 B1 | 8/2015 |
| KR | 10-1546560 B1 | 8/2015 |
| KR | 10-2015-0100707 A | 9/2015 |
| KR | 10-2015-0105462 A | 9/2015 |
| KR | 10-1549044 B1 | 9/2015 |
| KR | 10-1549051 B1 | 9/2015 |
| KR | 10-1549086 B1 | 9/2015 |
| KR | 10-2015-0119204 A | 10/2015 |
| KR | 10-2015-0120982 A | 10/2015 |
| KR | 10-2015-0120983 A | 10/2015 |
| KR | 10-2015-0121053 A | 10/2015 |
| KR | 10-1559525 B1 | 10/2015 |
| KR | 10-1560039 B1 | 10/2015 |
| KR | 10-2015-0122367 A | 11/2015 |
| KR | 10-2015-0123139 A | 11/2015 |
| KR | 10-2015-0126617 A | 11/2015 |
| KR | 10-2015-0127727 A | 11/2015 |

(56) References Cited

FOREIGN PATENT DOCUMENTS

| | | |
|---|---|---|
| KR | 10-1567098 B1 | 11/2015 |
| KR | 10-1571136 B1 | 11/2015 |
| KR | 10-2015-0138646 A | 12/2015 |
| KR | 10-2015-0138647 A | 12/2015 |
| KR | 10-2015-0140306 A | 12/2015 |
| KR | 10-2015-0143734 A | 12/2015 |
| KR | 10-1575056 B1 | 12/2015 |
| KR | 10-1575690 B1 | 12/2015 |
| KR | 10-2016-0005767 A | 1/2016 |
| KR | 10-1582822 B1 | 1/2016 |
| KR | 10-1585197 B1 | 1/2016 |
| KR | 10-1588463 B1 | 1/2016 |
| KR | 10-2016-0017071 A | 2/2016 |
| KR | 10-2016-0017072 A | 2/2016 |
| KR | 10-2016-0019944 A | 2/2016 |
| KR | 10-1592277 B1 | 2/2016 |
| KR | 10-1592378 B1 | 2/2016 |
| KR | 10-1594908 B1 | 2/2016 |
| KR | 10-2016-0029006 A | 3/2016 |
| KR | 10-1602931 B1 | 3/2016 |
| KR | 10-2016-0040603 A | 4/2016 |
| KR | 10-2016-0041667 A | 4/2016 |
| KR | 10-2016-0046022 A | 4/2016 |
| KR | 10-1610598 B1 | 4/2016 |
| KR | 10-1616405 B1 | 4/2016 |
| KR | 10-2016-0052590 A | 5/2016 |
| KR | 10-2016-0053114 A | 5/2016 |
| KR | 10-2016-0053384 A | 5/2016 |
| KR | 10-2016-0056004 A | 5/2016 |
| KR | 10-2016-0056005 A | 5/2016 |
| KR | 10-1618297 B1 | 5/2016 |
| KR | 10-1618523 B1 | 5/2016 |
| KR | 10-1622374 B1 | 5/2016 |
| KR | 10-1622388 B1 | 5/2016 |
| WO | WO-9517866 A1 * | 7/1995 .......... A61M 35/006 |
| WO | 00/74763 A2 | 12/2000 |
| WO | 02/06829 A2 | 1/2002 |
| WO | 2005/025413 A2 | 3/2005 |
| WO | WO-2007026340 A2 * | 3/2007 ............. A61B 5/446 |
| WO | 2007/068433 A2 | 6/2007 |
| WO | 2010/117625 A2 | 10/2010 |
| WO | 2011/067187 A1 | 6/2011 |
| WO | 2011/143016 A1 | 11/2011 |
| WO | 2011/143020 A1 | 11/2011 |
| WO | 2011/143022 A1 | 11/2011 |
| WO | 2011/143023 A1 | 11/2011 |
| WO | 2012/036697 A1 | 3/2012 |
| WO | 2012/100100 A2 | 7/2012 |
| WO | 2012/121695 A1 | 9/2012 |
| WO | 2013/020220 A1 | 2/2013 |
| WO | 2013/058879 A2 | 4/2013 |
| WO | 2013/082418 A1 | 6/2013 |
| WO | 2013/082427 A1 | 6/2013 |
| WO | 2013/109309 A1 | 7/2013 |
| WO | 2014/025393 A1 | 2/2014 |
| WO | 2014/111623 A1 | 7/2014 |
| WO | 2007/075279 A1 | 7/2017 |

OTHER PUBLICATIONS

Machine Translation of JP 2008-188302 from Global Dossier (Year: 2021).*
Machine Translation of KR-20080014461 (Year: 2021).*
European Summons to Oral Proceedings dated Nov. 17, 2020, issued European Patent Application No. 17853298.2-1115.
Korean Notice of Allowance dated Oct. 22, 2019, issued in Korean Patent Application No. 10-2016-0165891.
Korean Office Action dated Jul. 9, 2019, issued in Korean Patent Application No. 10-2019-0066148.
Extended European Search Report dated Sep. 19, 2019, issued in European Patent Application No. 17853298.2.
Chinese Office Action dated Mar. 3, 2021, issued in Chinese Patent Application No. 201780055391.9.
Indian Examination Report dated Apr. 12, 2021, issued in Indian Patent Application No. 201947014435.
Korean Office Action dated Apr. 4, 2019, issued in Korean Patent Application No. 10-2016-0165891.
European Partial Search Report dated Jun. 19, 2019, issued in European Patent Application No. 17853298.2.
European Examination Report dated Apr. 15, 2020, issued in European Application No. 17853298.2.
Korean Office Action dated Jan. 28, 2020, issued in Korean Application No. 10-2019-0066148.
Korean Office Action dated Apr. 2, 2020, issued in Korean Application No. 10-2019-0066148.
European Notice of Allowance dated Jun. 16, 2021; European Appln. No. 17 853 298.2-1122.

* cited by examiner

FIG. 5
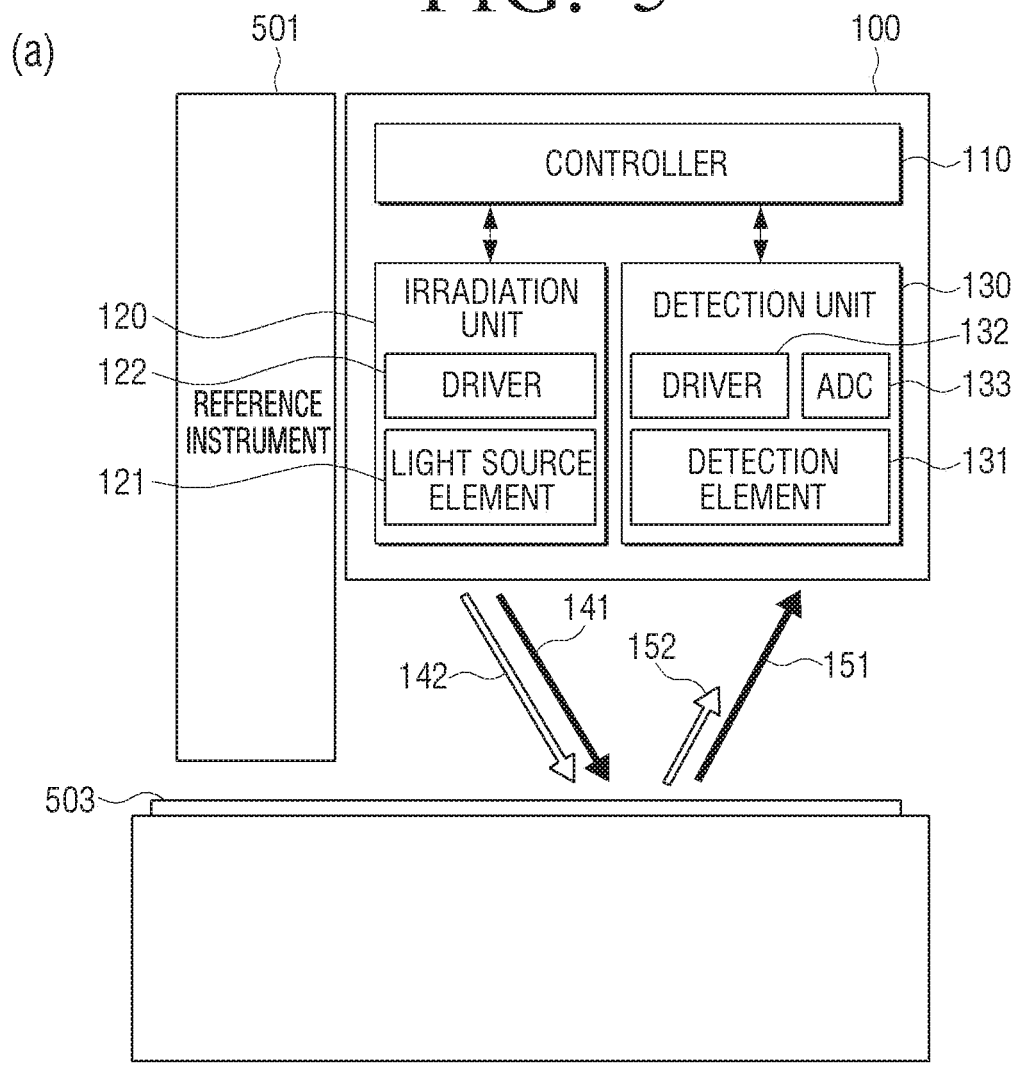
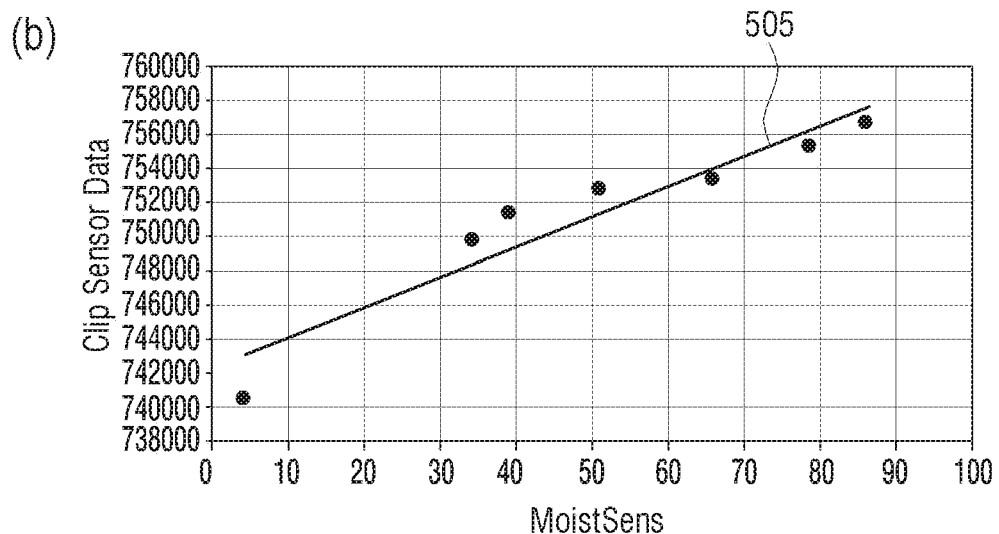

FIG. 29
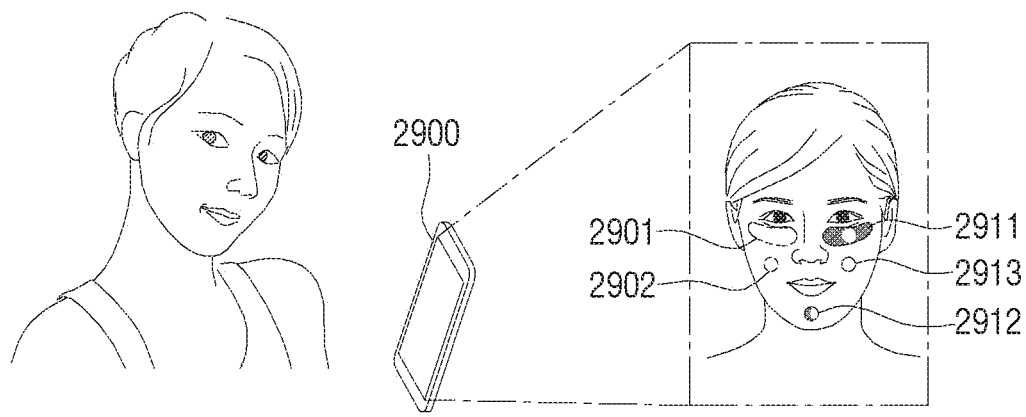
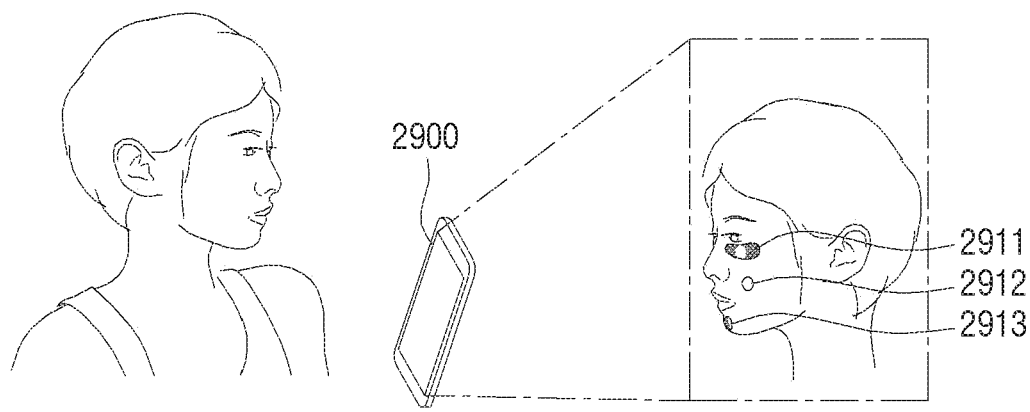
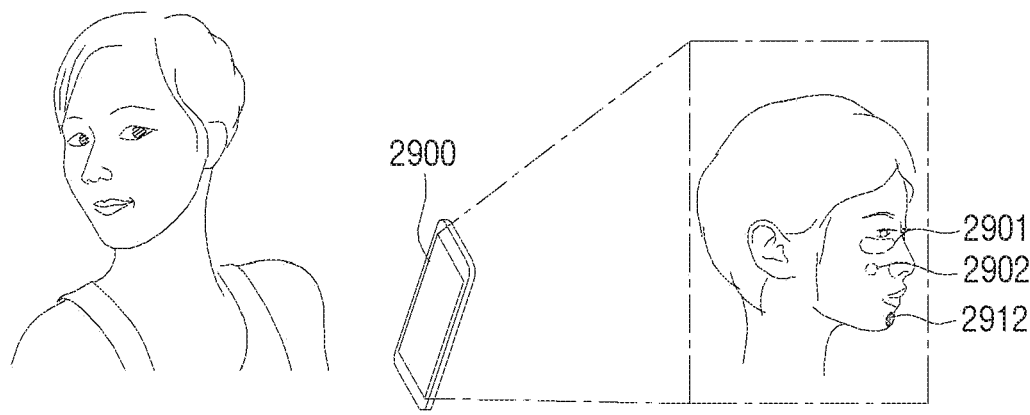

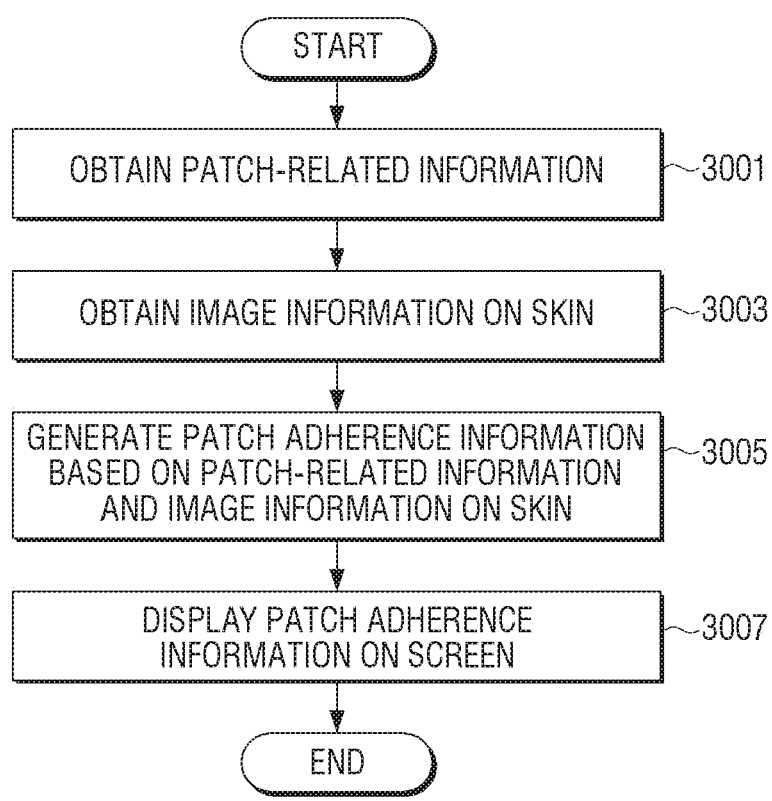

METHOD FOR MEASURING SKIN CONDITION AND ELECTRONIC DEVICE THEREFOR

FIELD OF THE INVENTION

Devices and methods consistent with what is disclosed herein relate to an electronic device, and more particularly, to a method for measuring skin condition, an electronic device thereof, and a micro needle patch on which the electronic device is mounted.

DESCRIPTION OF THE RELATED ART

When a physiologically active substance is injected into human skin by using injection needles, it may cause pain at the injection site, damage to the skin, bleeding, or infectious diseases caused by injection needles.

Therefore, recently, a method for delivering physiologically active substances using microneedles (or ultra-micro needles) into skin has been actively studied. The microneedles may have tens to hundreds of micro-diameters to penetrate the stratum corneum of the skin, which is the main barrier layer of a physiologically active substance.

In order to allow the physiologically active substance to be effectively delivered into the skin through the micro needles, a certain period of skin contact time may be required. Therefore, a micro-needle patch having one surface on which micro-needles capable of injecting physiologically active substances are arranged is recently used for safely adhering and maintain the micro-needle to the skin.

When the micro needle patch is adhered to the skin, the micro needles may penetrate the stratum corneum and reach the epidermal layer or the dermal layer below the stratum corneum.

When the micro needles are formed of a biodegradable material, the microneedles reaching the epidermal layer or the dermal layer may be melted into the skin after few minutes to few hours.

Even when the physiologically active substances are applied to the microneedles or physiologically active substances are stored inside the microneedles, the physiologically active substances may be absorbed into the skin as the microneedles reach the epidermal layer or the dermal layer.

The micro needle patch may usually be adhered to the skin along the curve of the skin with user's hands, but depending on user's doings or habits, the micro needle patch may not be adhered firmly to the skin.

In this case, the physiologically active substances provided through the micro needles cannot be sufficiently absorbed into the skin, so that the absorption rate of the physiologically active substances may be lowered.

Therefore, it is necessary to confirm whether the micro needle patch is well adhered to the skin or whether the physiologically active substances provided through the micro needles are sufficiently absorbed into the skin.

In addition, the technical problem to be solved in the disclosure is not limited to the above-mentioned technical problems, and other technical problems which are not mentioned can be clearly understood by those skilled in the art.

SUMMARY

According to an embodiment, there is provided a method for measuring skin condition of an electronic device including irradiating at least one light into skin to which a patch is adhered, detecting at least one reflective light based on an amount of moisture in the skin changed by physiologically active substances injected through the patch in response to the at least one irradiated light, generating patch adherence information indicating an adhesive state of the patch based on a detection result of the at least one reflective light, and providing the generated patch adherence information to an output unit or a communicator of the electronic device.

According to an embodiment, there is provided a method for measuring skin condition of an electronic device including irradiating at least one light into skin, detecting at least one reflective light reflected based on an amount of moisture in the skin in response to the at least one irradiated light, and identifying a moisture level of the skin based on the detection result.

According to an embodiment, there is provided an electronic device for measuring skin condition including an irradiation unit configured to irradiate at least one light into skin to which a patch is adhered, a detection unit configured to detect at least one reflective light based on an amount of moisture in the skin changed by physiologically active substances injected through the patch in response to the at least one irradiated light, and a controller configured to generate patch adherence information indicating an adhesive state of the patch based on a detection result of the at least one reflective light and provide the generated patch adherence information to an output unit or a communicator of the electronic device.

According to an embodiment, there is provided an electronic device for measuring skin condition including an irradiation unit configured to irradiate at least one light into skin, a detection unit configured to detect at least one reflective light reflected based on an amount of moisture in the skin, and a controller configured to identify a moisture level of the skin based on a detection result.

According to an embodiment, there is provided a microneedle patch including a non-conductive support contacting skin, microneedles arranged on a surface of the non-conductive support, physiologically active substances included in the microneedles and injected into the skin, and an electronic device configured to irradiate at least one light into skin below a patch adhered to skin, detect at least one reflective light based on an amount of moisture of the skin changed by the physiologically active substances injected into the skin through the patch in response to the at least one irradiated light, and generate patch adherence information indicating an adhesive state of the patch to skin based on at least one detection result.

According to an embodiment of the disclosure, it becomes possible to measure skin condition by irradiating light into skin.

Particularly, patch adherence information indicating an adhesive state of a patch to skin based on a moisture level of the skin is provided to a user. Accordingly, the user easily checks the adhesive state of the patch and manage the patch such as re-adhesion of the patch or the close adhesion of the patch.

In addition, the skin condition or the patch adhesive state according to a result of irradiating light is provided to a portable terminal regularly, or upon a user's request, customized skin management becomes possible continuously.

In addition, effects obtainable or predicted by the embodiments of the disclosure will be directly or implicitly disclosed in the detailed description of the embodiments of the disclosure. For example, various effects that are predicted according to embodiments of the disclosure will be disclosed within the following detailed description.

BRIEF DESCRIPTION OF THE DRAWINGS

FIG. 5 is a view illustrating an experiment for acquiring an equation for identifying a moisture level according to an embodiment of the disclosure;

FIG. 29 is a view illustrating an electronic device for providing patch adherence information according to another embodiment of the disclosure; and FIG. 30 is a flowchart to explain an electronic device to provide patch adherence information according to an embodiment of the disclosure.

DETAILED DESCRIPTION OF EXEMPLARY EMBODIMENTS

Figure 1:
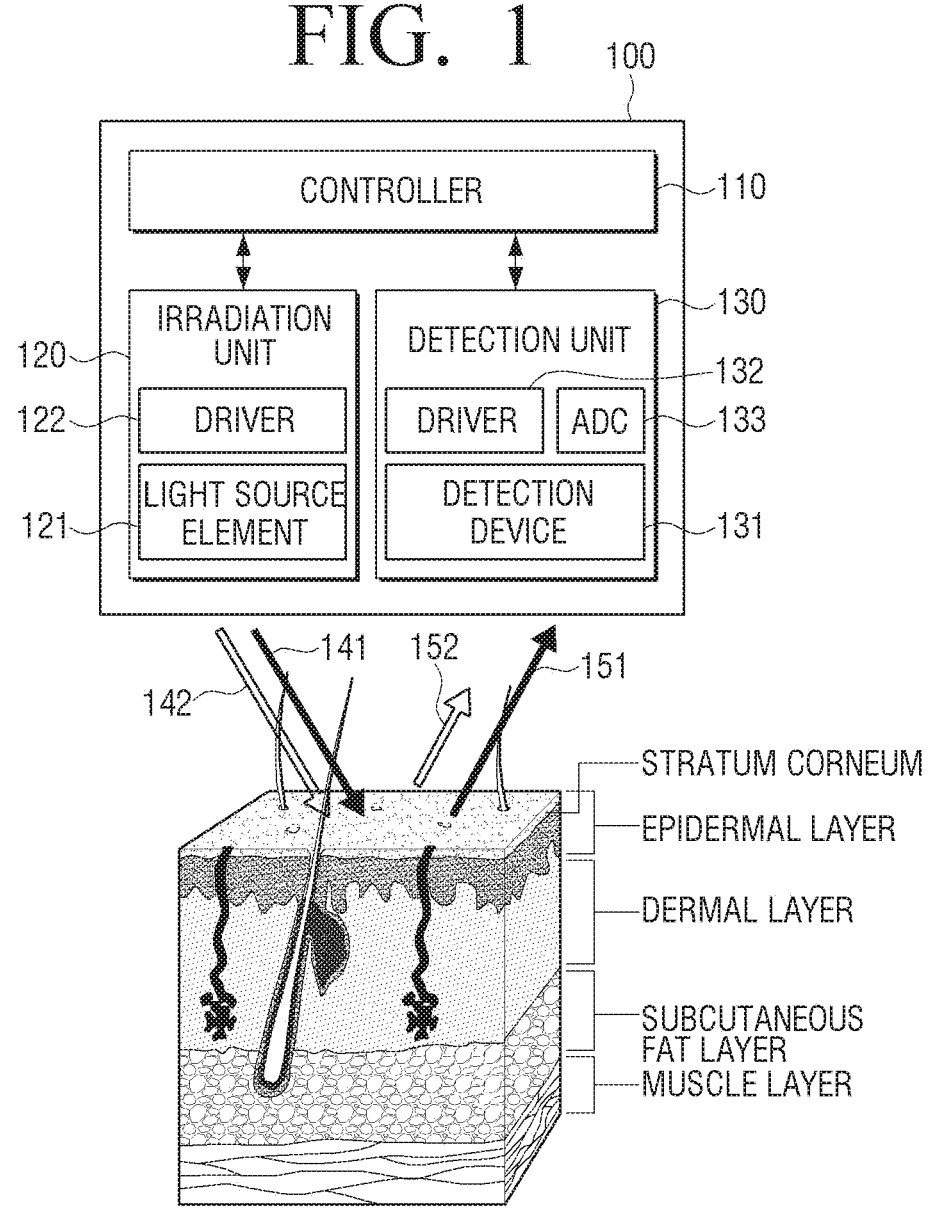
FIG. 1 is a view illustrating configuration of an electronic device configured to measure skin condition according to an embodiment of the disclosure.

It is to be understood that the disclosure herein is not intended to limit the scope to the described embodiments, but includes various modifications, equivalents, and/or alternatives of the embodiments. In the description of the drawings, like reference numerals refer to like elements throughout the description of drawings.

According to the disclosure, the expressions "include," "comprise," "including," and "comprising" indicate that one or more components, steps, operations, and elements exist or are added, and do not exclude the presence of additional features.

In the disclosure, the expressions "A or B," "at least one of A and/or B," or "one or more of A and/or B," and the like include all possible combinations of the listed items. For example, "A or B," "at least one of A and B," or "at least one of A or B" refers to (1) includes at least one A, (2) includes at least one B or (3) includes at least one A and at least one B.

Terms such as "first" and "second" may be used to modify various elements regardless of order and/or importance. Those terms are only used for the purpose of differentiating a component from other components. For example, the first user equipment and the second user equipment may represent different user equipment, regardless of order or importance. For example, without departing from the scope of the claims described in this disclosure, the first component may be referred to as a second component, and similarly, the second component may also be referred to as the first component.

When an element (e.g., a first constituent element) is referred to as being "operatively or communicatively coupled to" or "connected to" another element (e.g., a second constituent element), it should be understood that each constituent element is directly connected or indirectly connected via another constituent element (e.g., a third constituent element). However, when an element (e.g., a first constituent element) is referred to as being "directly coupled to" or "directly connected to" another element (e.g., a second constituent element), it should be understood that there is no other constituent element (e.g., a third constituent element) interposed therebetween.

The terminology used herein is for the purpose of describing particular embodiments and is not intended to be limiting the scope of other example embodiments. As used herein, the singular forms are used for convenience of explanation, but are intended to include the plural forms as well, unless the context clearly indicates otherwise. In addition, terms used in this specification may have the same meaning as commonly understood by those skilled in the art. General predefined terms used herein may be interpreted as having the same or similar meaning as the contextual meanings of the related art, and unless expressly defined herein, the terms are not to be construed as an ideal or overly formal sense. In some cases, the terms defined herein may not be construed to exclude embodiments of the disclosure.

FIG. 1 is a view illustrating configuration of an electronic device configured to measure skin condition according to an embodiment of the disclosure.

Referring to FIG. 1, an electronic device 100 may be configured to measure skin condition.

The electronic device 100 may be mounted on a patch according to an implementation method, or may be all or part of the electronic device 100 in different use. The various example embodiments of the electronic device 100 will be described in detail later.

The electronic device 100 may include a controller 110, an irradiation unit 120 and a detection unit 130.

The irradiation unit 120 may irradiate light into the skin, and change electrical energy into light energy. The irradiation unit 120 may include a light source device 121 and a driver 122 for driving the light source device 121. The light source device 121 may include at least one light emitting diode (LED), at least one laser diode (LD), or a combination thereof.

The irradiation unit 120 may irradiate at least one light into the skin by controlling the light source device 121. The irradiation unit 120 may irradiate light into the skin before a patch is adhered so as to measure a reference value. The irradiation unit 120 may irradiate light when the patch is adhered to the skin, or after the patch is removed from the skin.

The irradiation unit 120 may include the light source device 121 having various wavelengths according to the use of the electronic device 100.

The irradiation unit 120 may include the light source device 121 for emitting a reference light 141 and a measurement light 142 depending on the purpose. The reference light 141 and the measurement light 142 may be experimentally identified.

For an example embodiment, the wavelength of the reference light 141 may be a reference wavelength to be measured, for example, a light having a high reflectivity, which is not deeply absorbed into an object be measured may be the case. The measurement light 142 may be, for example, a light having a low reflectivity, which is relatively well absorbed into the object to be measured.

The reference light 141 and the measurement light 142 may be used for measuring the pigment of the skin (e.g., melanin of skin or erythema of skin).

When melanin of the skin is measured, mostly, the greater the amount of melanin, the close the skin color is to black, and the smaller the amount of melanin, the closer the skin color is to while. Based on the wavelength absorption rate, and the reflectivity of melanin, the wavelength of the light source device may be identified. A near infrared ray (NIR) value between 780 mλ and 3000 mλ may be used as the wavelength of the reference light 141. Further, the value of the red visible light ray between 620 mλ and 780 mλ may be used as the wavelength of the measurement light 142.

When erythema of the skin is measured, the wavelength of the light source device may be identified based on the wavelength absorption rate or the reflectivity of the erythema. Erythema may be characterized in that the skin is turned into red color due to expansion of blood vessels. Therefore, the value of the red visible light ray between 620 nmλ and 780 nmλ, which has a large reflectivity for red, may be used as the wavelength of the reference light 141. Further, the value of the green visible light ray between 500 nmλ and 570 nmλ may be used as the wavelength of the measurement light 142.

For another example embodiment, the wavelength of the reference light 141 may be a reference wavelength of an object to be measured, and a light having a small change in reflectivity depending on an object to be measured (a ratio of an intensity of an irradiated wavelength to an intensity of a reflected wavelength). The wavelength of the measurement light 142 may be a light having a greater change in reflectivity depending on an object to be measured.

The reference light 141 and the measurement light 142 may be used when the electronic device 100 is configured to measure the moisture level or the degree of hydration of the skin. That is, the wavelengths of the light source device may be identified based on the wavelength absorption rate or the reflectivity depending on the amount of moisture of the skin.

Figure 2:
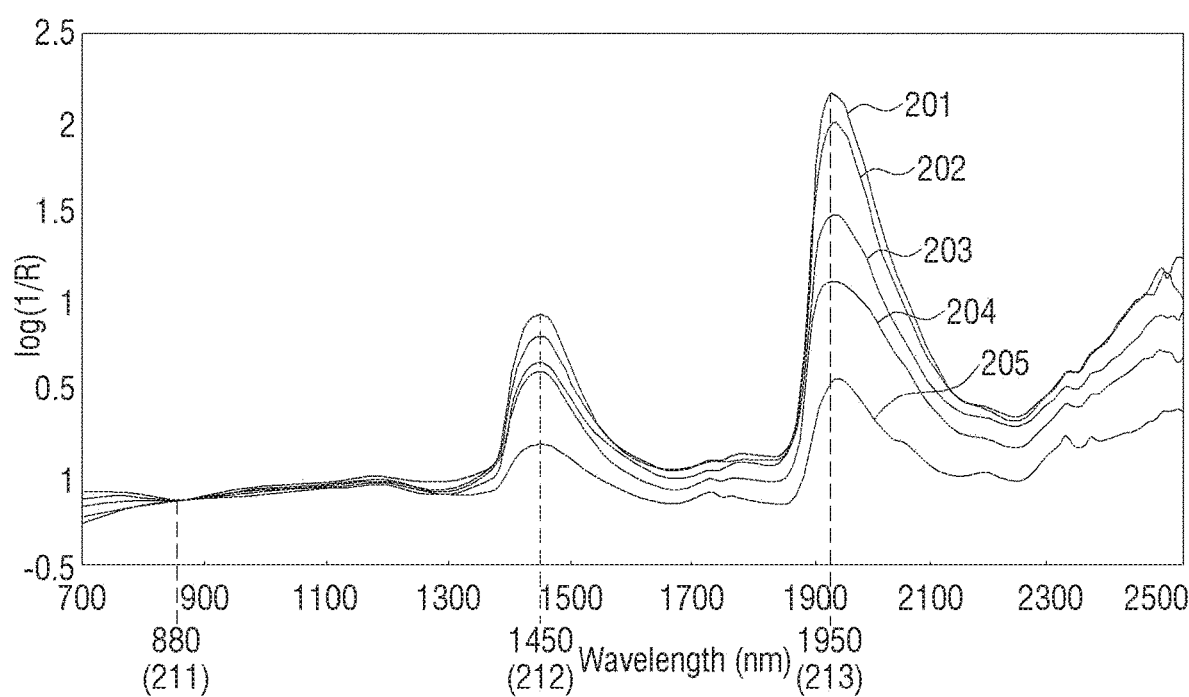
FIG. 2 is a view illustrating graphs to show a reflectivity by wavelength depending on a moisture level of skin according to an embodiment of the disclosure.

FIG. 2 is a view illustrating graphs showing a reflectivity by wavelength according to the moisture level of the skin. In the table of FIG. 2, an x-axis represents a wavelength value and a y-axis represents a logarithm of a reciprocal of a skin reflectivity by wavelength.

A plurality of graphs 201 to 205 may show a skin reflectivity by wavelength as time passes after a sample (e.g., skin or filter paper) is sufficiently wetted with water (e.g., saline solution, etc.).

Graph 201 may show the reflectivity by wavelength immediately after the sample is wetted with water for 1 hour. Graph 202 may show the reflectivity by wavelength after the sample is wetted with water for 4 hours. Graph 203 may show the reflectivity by wavelength after 9 hours elapses, graph 204 may show the reflectivity by wavelength after 21 hours, and graph 205 may show the reflectivity by wavelength after 24 hours elapses.

In each graph, it can be seen that lower the moisture level in the sample, the less the wavelength is absorbed, and the higher the reflectivity. In other words, the less a y-axial value, the higher reflectivity because the y-axial value is a logarithm of a reciprocal of the reflectivity. In other words, the smaller the y-axial value, the lower the absorption rate corresponding to the reflectivity.

Referring to the actually measured graphs 201 to 205, it can be seen that the reflectivity by wavelength is fixed regardless of the moisture level of the sample at the point of 880 nmλ 211. It can also be seen that the change in the reflectivity by wavelength may be large in accordance with the change in the moisture level of the sample at the point of 1450 nmλ 121, and at the point of 1950 nmλ 213.

Experimentally, the short wavelength (approximately, 880 nmλ) of the near infrared ray (NIR) may be selected as the reference light of the light source device 121 and the long wavelength of the near infrared ray (NIR) (approximately, 1450 nmλ or 1950 nmλ) may be selected as the measurement reference light. Preferably, the long wavelength of the near-infrared ray used as the measurement light may be selected to be about 1450 nmλ in consideration of the cost efficiency.

Based on the experimental result, the light source device 121 may include an LED that emits near infrared rays of about 880 nmλ as the reference light, and an LED that emits near infrared rays of about 1450 nmλ as the measurement light.

The detection unit 130 may be configured to detect light, and change light energy to electrical energy. For example, the detection unit 130 may include at least one photo diode (PD) as a detection device 131 (or, a light sensor). The detection unit 130 may include a driver 132 for driving the detection device 131, and an analog to digital converter (ADC) 133 for converting a detection result into a digital value. The ADC 133 may be an additional module or a part of the controller 110.

The detection device 131 may include at least one PD depending on a detection range. For example, when it is possible for one PD to detect all wavelengths of reflective lights respectively corresponding to a reference light and a measurement light, the detection device 131 may include one PD. However, the detection range of the PD may vary. For example, the detection range of one PD may be between about 320 nm and 1100 nm, and the detection range of the other PD may be between about 1200 nm and 2200 nm. In this case, the detecting device 131 may include a plurality of PDs for respectively detecting the wavelength of the reflective light corresponding to the reference light and the wavelength of the reflective light corresponding to the measurement light.

Referring to FIG. 1, the detection unit 130 may detect a reflective light 151 corresponding to the reference light 141, and a reflective light 152 corresponding to the measurement light 142. Referring to FIG. 1, when the reference light 141 and the measurement light 142 are irradiated at the similar intensity, the measurement light 142 may be absorbed well relatively to the reference light 141, and thus the intensity of the reflectivity light 152 corresponding to the measurement light 142 may be smaller than the intensity of the reflective light 151 corresponding to the reference light 141.

A memory (not shown) may store an algorithm for identifying the moisture level of skin according to the detection result by the detection unit 130.

The memory (not shown) may store an algorithm for generating patch adherence information indicating the adhesive state of the patch based on the measured moisture level. The memory (not shown) may permanently or temporarily store the detection result and the generated patch adherence information.

The controller 110 may control the irradiation unit 120 to irradiate at least one light into the skin. The controller 110 may detect at least one reflective light based on the amount of moisture in the skin by controlling the detection unit 130.

Figure 3:
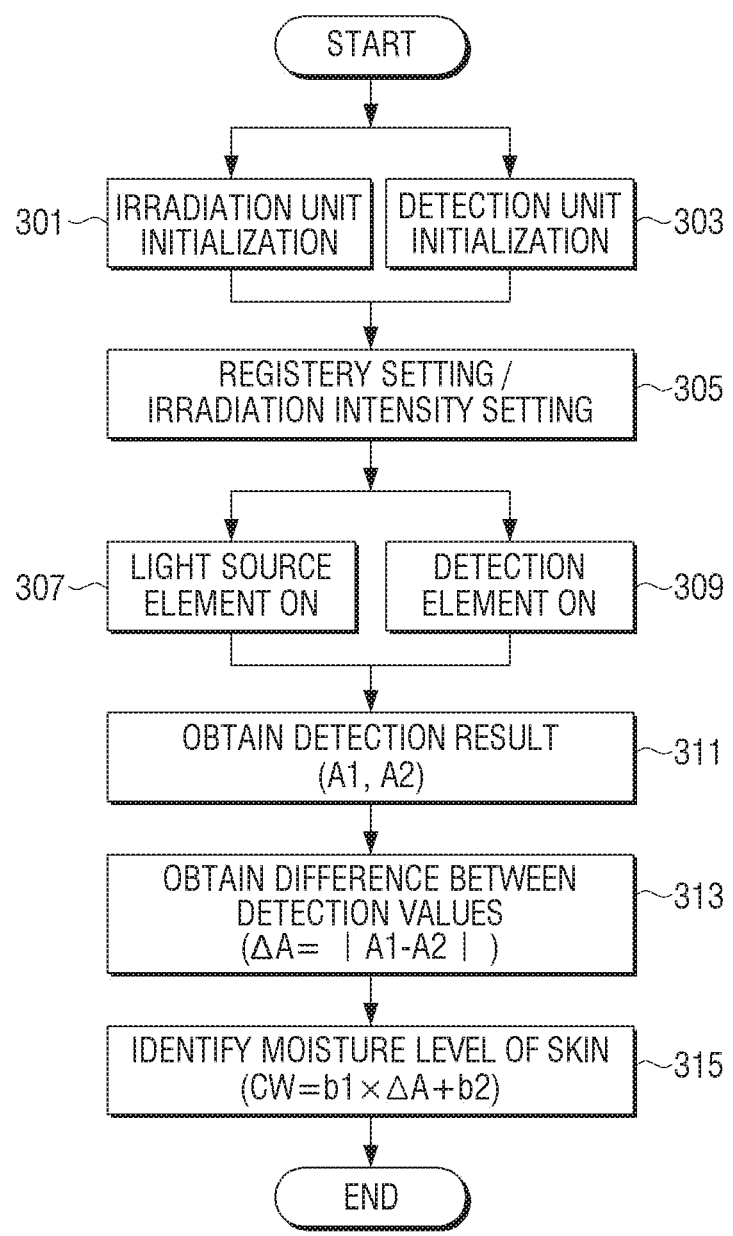
FIG. 3 is a flow chart showing a process of identifying a moisture level of skin by a controller of an electronic device according to an embodiment of the disclosure.

FIG. 3 is a flow chart showing a process of identifying a moisture level of skin by a controller 110 of an electronic device 100 according to an embodiment of the disclosure.

At operations 301 and 303 of FIG. 3, the controller 110 may initialize the irradiation unit 120 and the detection unit 130. For example, the controller 110 may initialize the driver 122 included in the irradiation unit 120, the driver 132 included in the detection unit 130 and the ADC 133.

At operation 305, the controller 110 may set a register for driving the irradiation unit 120 and the detection unit 130. An example embodiment of the register may be a register provided by an AFE4403 chip, but the type of chip is not limited thereto.

For example, the controller 110 may set a timer for a light source irradiation time of the irradiation unit 120 and a light source detection time of the detection unit 130 and an irradiation intensity.

Preferably, the light source irradiation time may be between 10 us and 10 ms, and the light source detection time may be, for example, between 1 us and 10 ms, but is not limited to the above example. In this case, the light source detection time may be set shorter than the light source irradiation time considering a delay time according to charge or discharge of a capacitor connected to the circuit of the light source device 121.

The light source irradiation intensity may be a current between 10 mλ to 1 A, but is not limited to the above-described example.

At operations 307 and 309, the controller 110 may turn on the light source device 121 and the detection device 131 by controlling the driver 122 of the irradiation unit 120 and the driver 132 of the detection unit 130, and drive each driver according to the set timer or the irradiation intensity.

The irradiation unit 120 may irradiate a first light which is the reference light and a second light which is the measurement light.

At operation 311, when the first reflective light and the second reflective light reflected based on the amount of moisture in the skin are detected through the detection unit 130, the controller 110 may obtain the detection intensity value of the first reflective light and the detection intensity value of the second reflective light as a detection result. Detecting reflective light based on the amount of moisture in the skin means that the part of the first light and the part of the second light are absorbed into the moisture of the skin, and the first reflective light and the second reflective light having a lower intensity are detected.

The detection unit 130 may obtain the detection intensities of the first reflective light and the second reflective light as gain values. In this case, the gain values may be within various ranges and units depending on the type of LED, wavelength, light intensity, LED current consumption, and mechanism configuration.

Figure 4:
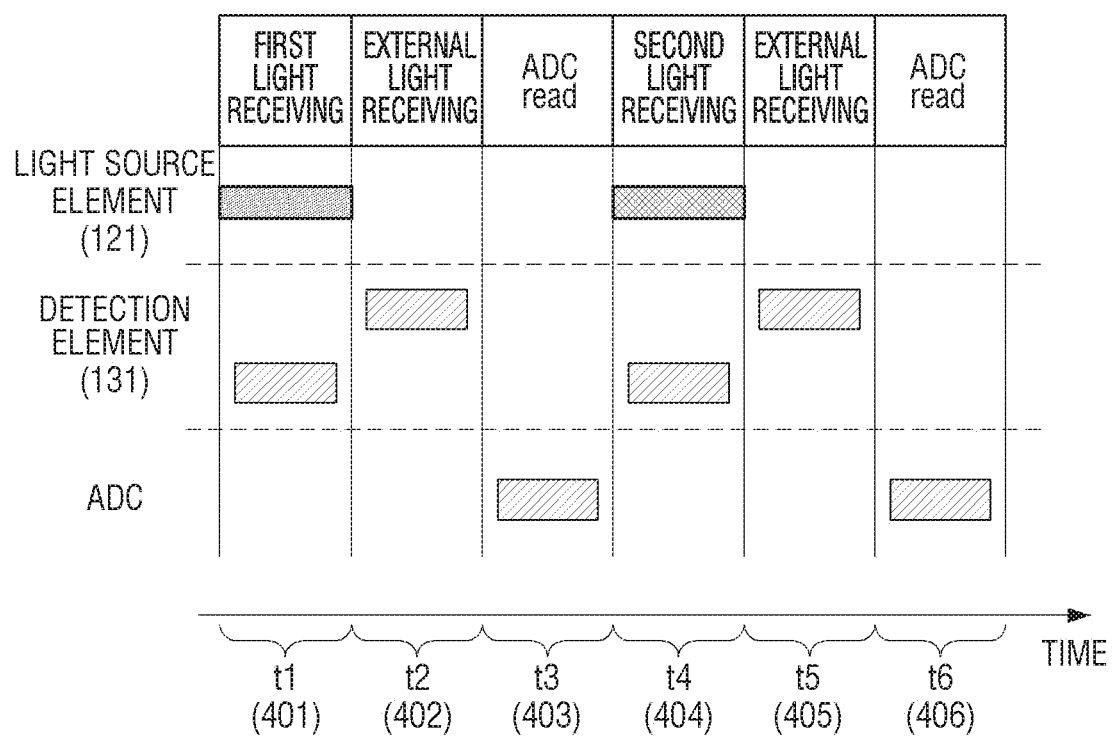
FIG. 4 is a view illustrating a process of obtaining a detection result of reflective light by an electronic device according to an embodiment of the disclosure.

FIG. 4 is a view illustrating a process of obtaining a detection result of reflective light of an electronic device 100 according to an embodiment of the disclosure.

FIG. 4 shows an example in which a first light and a second light are measured according to time, and the first light and the second light may be light having different wavelength values. One of the first light and the second light may be the reference light described above, and the other may be the measurement light as described above.

Referring to FIG. 4, during a first time period t1 401, the light source device 121 of the irradiation unit 120 may irradiate the first light, and the detection device 131 of the detection unit 130 may detect the first reflective light reflected corresponding to the irradiated first light. When the light source device 121 irradiates the first light, a delay time may be required until the irradiation intensity reaches a certain value, and thus the detection time of the detection device 131 may be relatively shorter than the irradiation time of the light source device 121.

Referring to FIG. 4, during a second time period t2 402 of FIG. 4, the detection device 131 may detect external light. The detection device 131 cannot detect light of a specific wavelength, and the light detected during the first time period t1 401 by the detection device 131 may include the first light and the external light. Accordingly, in order to extract only the first light from the light detected during the first time period t1 401, except for the external light, the detection device 131 may perform an additional job for detecting the external light.

Referring to FIG. 4, during a third time period t3 403, the ADC of the detection unit 130 may obtain a gain value as an intensity of the reflected first light, except for the external light detected during the second time period t2 402, from the light detected during the first time period t1 401, and convert the gain value into a digital value. For example, the ADC may convert the intensity of the reflected first light into 16 bit values, but is not limited thereto.

Referring to FIG. 4, the second light may be measured during a fourth time period t4 404 and a fifth time period t5 406 of FIG. 4 in the similar manner as the case during the first time period t1 401 to the third time period t3 403.

During the fourth time period t4 404 of FIG. 4, the light source device 121 of the irradiation unit 120 may irradiate the second light, and the detection device 131 of the detection unit 130 may detect the second reflective light reflected corresponding to the irradiated second light.

During the fifth time period t5 405, the detection device 131 may detect the external light.

During a sixth time period t6 406 of FIG. 4, the ADC of the detection unit 130 may obtain a gain value as an intensity of the second reflective light, except for the external light detected during the fifth time period t5 405, from the light detected during the fourth time period t4 404, and convert the gain value into a digital value.

For ease of explanation of FIG. 4, the first time period t1 401 to the sixth time period t6 406 are described in order, but each step is not limited to the time order. For example, the first light and the second light may be received after the external light is received, and the external light may be received after the first light and the second light are received.

Referring to FIG. 3, at operation 311, the controller 110 may obtain a first detection value indicating the intensity of the first reflective light corresponding to a reference light, and a second detection value indicating the intensity of the second reflective light corresponding to a measurement light.

At operation 313, the controller 110 may obtain a difference value between the first detection value and the second detection value.

The control unit 110 may substitute the obtained difference value into the formula prepared and stored in the memory (not shown) to identify the moisture level of the skin (or the hydration degree of the skin, the concentration of water of the skin, the amount of moisture of the skin, etc.)

The following shows Equation (1) for identifying water content C W of skin.

[Equation 1]

In Equation (1), $\Delta A$ is a difference value between a first detection value and a second detection value.

Further, b1 is a proportional coefficient for $\Delta A$, and b2 is an intercept for $\Delta A$.

Equation (1) can be obtained by a moisture measuring device using an existing impedance and a result of repeated experiments.

FIG. 5 is a view illustrating an experiment for acquiring an equation for identifying a moisture level according to an embodiment of the disclosure.

In (a) of FIG. 5, the experimenter may measure the degree of moisture in a sample 503 using a reference instrument 501 and the electronic device 100 of the disclosure.

In (a) of FIG. 5, as the sample 503, a filter paper wetted with a saline solution may be used.

In this case, the experimenter may measure moisture level C ref of the sample 503 using the reference instrument 501 for measuring moisture by impedance. The reference instrument 501 for measuring moisture by impedance may be, for example, a moistsense device or a corneometer as a well-known instrument, but is not limited to the above-described examples.

While measuring moisture using the reference instrument 501, the experimenter may irradiate the reference light 141 and the measurement light 142 to the sample 503 using the electronic device 100, and obtain a first detection value indicating the intensity of the first reflective light 151 corresponding to the reference light 141 reflected based on the amount of moisture in the sample 503. The experimenter may obtain a second detection value indicating the intensity of the second reflective light 152 corresponding to the measurement light 142 reflected based on the amount of moisture in the sample 503.

The experimenter may regularly measure the sample 503 according to a wet method or a dry method. The wet method may be a method of measuring the degree of moisture of the sample 503 and the intensity of the reflective light at regular intervals while increasing the amount of moisture of the dried sample 503, and the dry method may be a method of measuring the degree of moisture of the sample 503 and the intensity of the reflective light at regular intervals after sufficiently moistening the sample 503.

The table of (b) of FIG. 5 shows the results of measurement of the moisture level C ref at a predetermined period (e.g., about 5 minutes) as the sample 503 is dried by using the dry method, and calculation of a difference value $\Delta A$ ref between the first detection value and the second detection value of the sample.

The x-axis represents the moisture level C ref measured at regular intervals using the reference instrument 501, and the y-axis represents $\Delta A$ ref, which is the difference between the first detection value and the second detection value. The graph 505 of the table shows a regression line derived in consideration of respective corresponding points of C ref and $\Delta A$ ref at regular intervals.

In FIG. 5, the tilt of the regression line may correspond to the value b1 in equation (1), and the intercept of the regression line may correspond to the value b2.

When the equation (1) is set, the controller 110 may acquire a first detection value indicating the intensity of the first reflectivity light corresponding to the reference light and a second detection value indicating the intensity of the second reflective light corresponding to the measurement light. As in the operation 315 of FIG. 3, the first detection value and the second detection value may be substituted into equation (1) to identify the moisture content C W of the skin.

In the disclosure, the moisture content C W has been derived according to the results of the experiment of FIG. 5. However, this is only an example, and by using various kinds of equations and experimental methods, it is possible to identify the moisture level of the skin using a reflective light.

Figure 6:
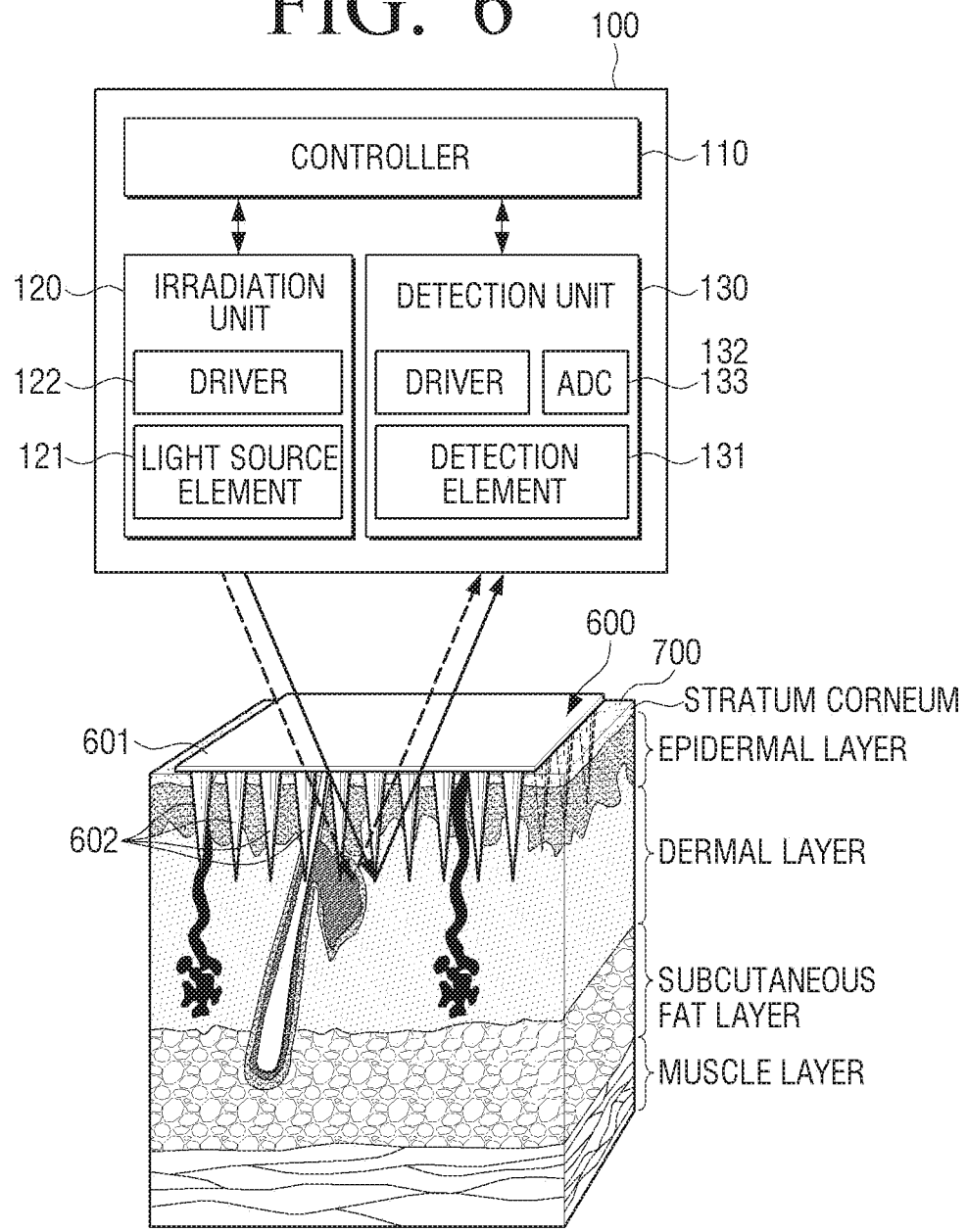
FIG. 6 is a view illustrating a micro needle patch on which an electronic device is mounted according to an embodiment of the disclosure.

FIG. 6 is a view illustrating a micro needle patch 600 on which an electronic device 100 is mounted according to an embodiment of the disclosure.

Referring to FIG. 6, for ease of explanation, an electronic device 100 and a micro needle patch 600 have been illustrated separately, but in the actual implementation, the electronic device 100 may be part of the micro-needle patch 600, and may be disposed on the upper surface, on the lower surface, or inside of the micro needle patch 600.

Referring to FIG. 6, the micro needle patch 600 may include a support 601, micro needles 602 and an electronic device 100.

The support 601 may provide a plane in which the micro needles 602 are arranged, and the electronic device 100 may be disposed in one area of the support 601.

The support 601 may be formed of a non-conductive material, and have flexibility so that the micro needle path 600 may be firmly adhered to skin 700 along a curve of the skin 700.

The support 601 may include at least one of a needle sheet (or a base sheet) in which the micro needles 602 are arranged and a patch sheet (or an adhesive sheet) adhered to the skin, and may be formed of a transparent material.

Examples of the material of the support 601 include at least one of a cellulose resin, a polyester resin such as polyethylene terephthalate (PET) and polyethylene naphthalate (PEN), a polyethylene resin, a polyvinyl chloride resin, a polycarbonate (PC), a polyethylene sulfone (PES), a polyether ether ketone (PEEK), a polyphenylene sulfide (PPS), and a hydrocolloid, or a combination thereof.

The micro needles 602 may be arranged on the needle sheet of the support 601, and may include physiologically active substances. The physiologically active substance may be, for example, a compound or a molecule that induces a biological reaction, and may include a therapeutic substance, or a non-therapeutic substance such as a cosmetic substance, an anesthesia material, or a dietary use.

The micro needles 602 may be formed of a biodegradable material, which is an example of a physiologically active substance.

The biodegradable material may be a substance that can be decomposed by body fluids or microorganisms in body.

The biodegradable material may be, for example, a complex polysaccharide consisting of amino acid and uronic acid, and may contain hyaluronic acid capable of containing 100 to 1,000 times the weight of its own weight.

Examples of biodegradable materials include sodium hyaluronate, lactos, DW-EGF (sh-Oligopeptid-1), polyester, polyhydroxyalkanoate (PHAs), polyhydroxy acid, poly (3-hydroxypropionate), poly (3-hydroxybutyrate-co-valerate, PHBV), poly (3-hydroxypropionate, PHP), poly (3-hydroxyhexanoate, PHH), poly (4-hydroxyacid), poly (4-hydroxybutyrate), poly (4-hydroxyvalerate), poly (4-hydroxyhexanoate), poly (lactide-co-glycolide) (PLGA), polydioxanone, polyorthoester, polyetherester, polyanhydride, poly (Trimethylene carbonate), poly (iminocarbonate), poly (tyrosine), polyoxyethylene (polyoxyethylene), polyoxyethylene (glycolic acid-co-trimethylene carbonate), polyphosphoester, polyphosphoester urethane, polycarbonate, poly (tyrosine arylate), polyalkylene oxalate, polyphosphazene, PHA-PEG, ethylene vinyl alcohol copolymer (EVOH), polyolefins, polyisobutylene and ethylene-alpha olefin copolymers, styrene-isobutylene-styrene triblock copolymers, acrylic polymers and copolymers, vinyl halide polymers and copolymers, polyvinyl chloride, polyvinyl ether, polyvinyl methyl ether, polyvinylidene halide, polyvinylidene fluoride, polyvinylidene chloride, polyfluoroalkene, polyperfluoroalkene, polyacrylonitrile, polyvinyl ketone, polyvinyl aromatics, Polystyrene, polyvinyl ester, polyvinyl acetate, acrylonitrile-styrene copolymers, ABS resins and ethylene-vinyl acetate copolymers, polyamides, alkyd resins, polyoxymethylene, polyimides, polyethers, polyacrylates, polymethacrylates, A mixture of at least one of polyacrylic acid-co-maleic acid, chitosan, dextran, cellulose, heparin, alginate, inulin, starch and glycogen, a combination thereof or a combination of two or more thereof.

In various embodiments, the microneedles 602 may be formed of a non-conductive material, such as a polymeric or ceramic based material. In this case, the physiologically active substance may be stored inside the microneedles 602 or inside the support 601.

In addition, the physiologically active substance may be coated with a thermosensitive polymer in a nano-capsule form. In this case, when the nano-capsule is injected into the skin at a predetermined depth to reach at a certain temperature, the applied polymer may be melted and the physiologically active substance in the capsule may be discharged. In the case of using a nano-capsule, the absorption amount and the absorption rate of the physiologically active substance may be further improved.

The micro needles 602 may have a conic shape as shown.

Alternatively, the microneedles 602 may have a pyramidal shape, a bullet shape, or a general needle shape with a certain diameter from the base and a pointed tip.

The height of the microneedles 602 may be appropriately set to reach the epidermal layer or the dermal layer below the stratum corneum.

As an example, human skin may include a stratum corneum (<20 μm), an epidermal layer (<100 μm) and a dermal layer (300 μm to 2,500 μm) from the epidermis. Therefore, in order to deliver skin cosmetic ingredients or medicines without pain to a specific skin layer, the diameter of the ends of the micro needles may be within 30 μm, and the height of the micro needles may be 50 μm to 2,000 μm so as to reach the epidermal layer or the dermal layer below the stratum corneum.

The electronic device 100 may include all or a part of the electronic device 100 of FIG. 1. For an example, the electronic device 100 may be formed on the surface of the support 601. The electronic device 100 may be formed by a conventional patterning process using an etching reaction and a photosensitive resin after laminating the metal material on the surface of the support 601. Alternatively, the electronic device 100 may be formed on the surface of the support 601 by a sputtering or evaporation method using a mask exposing a region where a metal material is to be deposited.

The irradiation unit 120 of the electronic device 100 may irradiate at least one light into the patch-adhered skin. For example, the irradiation unit 120 of the electronic device 100 may irradiate a reference light having a wavelength of 1450 nm and a measurement light having a wavelength of 880 nm. The description on how to obtain the wavelength values of the reference light and the measurement light will not be repeated.

The detection unit 130 of the electronic device 100 may detect at least one reflective light reflected based on the amount of moisture in the skin in response to the irradiated light. At least one reflective light may include a first reflective light corresponding to a reference light and a second reflective light corresponding to a measurement light.

The controller 110 of the electronic device 100 may identify the amount of moisture in the patch-adhered skin based on the detection result of at least one reflective light. For example, the controller 110 of the electronic device 100 may identify the amount of moisture in the skin based on a difference value between the intensity of the first reflective light and the intensity of the second reflective light.

Figure 7:
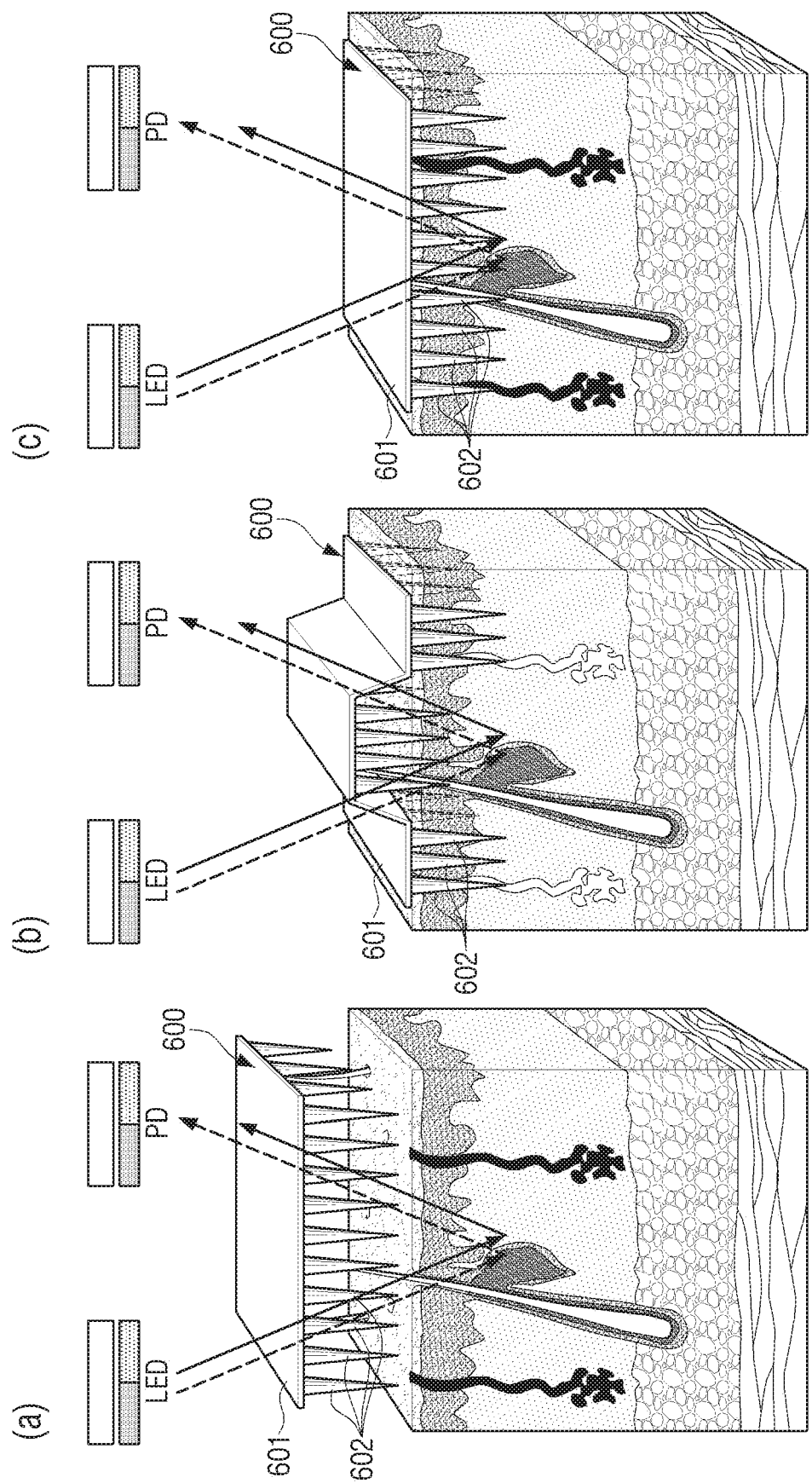
FIG. 7 is view illustrating a process of measuring skin condition by using a micro needle patch on which an electronic device is mounted according to an embodiment of the disclosure.

FIG. 7 is view illustrating a process of measuring skin condition by using a micro needle patch 600 on which an electronic device 100 is mounted according to an embodiment of the disclosure.

FIG. 7 (a) is a view illustrating a state before the micro needle patch 600 is adhered.

FIG. 7 (b) is a view shows that only a part of the micro needle patches 600 is adhered to the skin and only a part of the micro needles 602 reaches the epidermal layer or the dermal layer under the stratum corneum.

FIG. 7 (c) shows that all or most of the microneedle patches 600 are closely adhered to the skin so that all or most of the microneedles 602 reach the epidermal layer or the dermal layer below the stratum corneum.

When the micro needle patch 600 is closely adhered to the skin, the biodegradable material (e.g., hyaluronic acid) constituting the micro needles 602 may be melted into the skin (e.g., in the dermal layer).

When the electronic device 100 is mounted on the microneedle patch 600, the electronic device 100 may irradiate at least one light into skin under the patch adhered to the skin, and detect at least one reflective light corresponding to the irradiated light.

The moisture level of the skin may vary depending on the extent to which the physiologically active substance of the micro needle patch 600 is absorbed and dissolved into the skin.

The amount of moisture in the skin before the micro needle patch 600 are adhered to the skin as shown in FIG. 7 (a) may be smaller than the amount of moisture in the skin when only a part of the micro needle patch 600 is adhered and only a part of the physiologically active substances is absorbed into the skin as shown in FIG. 7 (b). The amount of moisture in the skin of FIG. 7 (b) may be less than the amount of moisture in the skin when the micro needle patch 600 is firmly adhered and the entire physiologically active substance is absorbed into the skin as shown in FIG. 7 (c).

Referring to FIG. 7 (a), FIG. 7 (b) and FIG. (c), when the electronic device 100 measures skin with a different moisture level, the moisture levels according to the detection results of at least one reflective light reflected based on the moisture levels of the skin may be calculated differently.

The electronic device 100 may generate patch adherence information indicating the extent to which the patch has adhered to the skin based on the moisture level in each of FIG. 7 (a), FIG. 7 (b) and FIG. 7 (c).

Generating the patch adherence information may include selecting or identifying one of a plurality of pieces of patch adherence information depending on the degree of moisture. In addition, generating the patch adherence information may include generating new patch adherence information according to the degree of moisture using a pre-prepared data generation algorithm.

For example, a patch table indicating patch adherence information mapped to a moisture level may be stored in a memory (not shown). The patch adherence information may be expressed by 2-bit information, texts or images, or may be expressed in various other forms of contents and data.

According to various embodiments, the degree of moisture may be expressed, for example, in percent (%).

In this case, when the degree of moisture is a value in a first range (e.g., 70% to 95%), the electronic device 100 may generate patch adherence information including information indicating that the micro needle patch 600 is closely adhered. The feature that the patch is adhered closely means that most (about 80% or more) of the micro needle 602 is absorbed and dissolved into the skin.

In this case, when the degree of moisture is a value in a second range (e.g., 30% to 70%), the electronic device 100 may generate patch adherence information including information indicating that the micro needle patch 600 is partly adhered. The feature that the patch is adhered partly means that part (about 30% to 80%) of the micro needle 602 is absorbed and dissolved into the skin.

Further, when the degree of moisture is a value in a third range (e.g., 5% to 30%), the electronic device 100 may generate patch adhesive information including information indicating that the micro needle patch 600 is not adhered. The feature that the patch is not adhered means, for example, that only a part of the micro needle (between about 0% and 30%) is absorbed and dissolved into the skin.

The patch adherence information identified according to the above-described range is only an example, but various ranges and patch adherence information may be generated according to the results of the implementation and the experiment.

According to various embodiments, it is possible to generate patch adherence information including the degree of change in moisture of the skin due to patch adherence.

For example, the electronic device 100 may identify the moisture level of the skin before or after patch adhesion, respectively, and generate patch adherence information indicating the change in the moisture level based on the difference between the identified moisture levels. The electronic device 100 may identify the moisture level of the skin at a predetermined period, and generate information indicating the change in the moisture level of the skin by time as patch adherence information.

The electronic device 100 may provide the generated patch adherence information to a user through an output unit (not shown) or a communicator (not shown). For example, when the electronic device 100 includes the communicator (not shown), the electronic device 100 may provide the generated patch adherence information to a user terminal (not shown) disposed at the outside through the communicator (not shown). The user may display the received patch adherence information though a display (not shown) of the user terminal (not shown).

When the display (not shown) is included in the electronic device 100 as the output unit (not shown), the electronic device 100 may provide the patch adherence information to the output unit (not shown).

Various example embodiments in which a user terminal provides patch adherence information and an example embodiment in which the electronic device 100 outputs the patch adherence information will be described with reference to FIG. 15, and thus the detailed description will be omitted.

Figure 8:
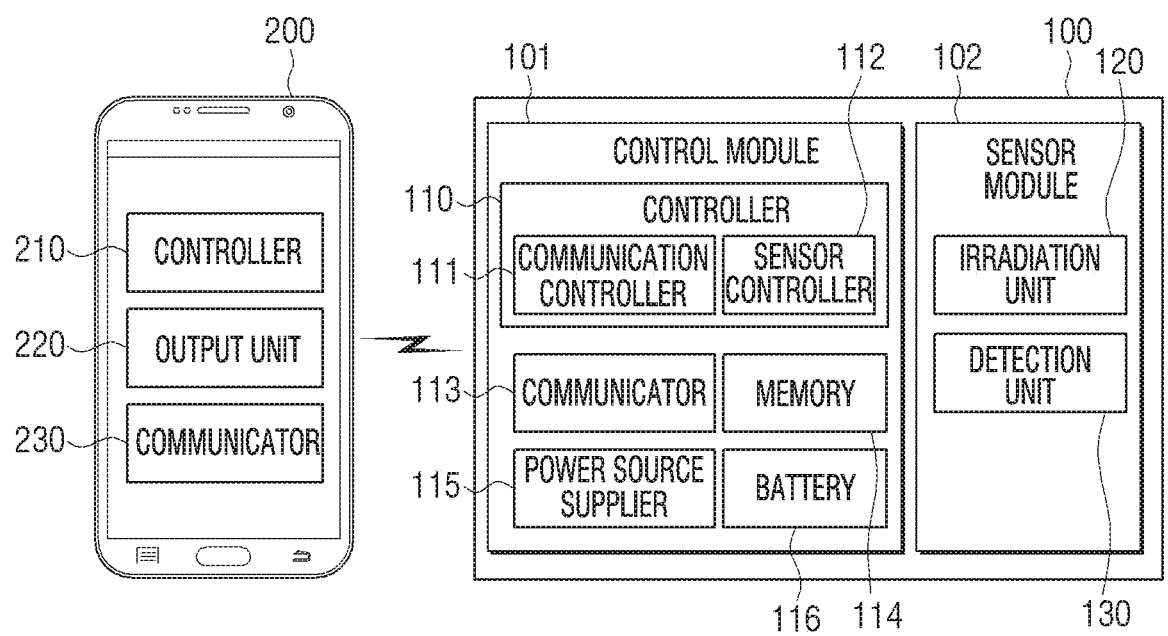
FIG. 8 is a view illustrating a system for measuring an adhesive state of a patch according to an embodiment of the disclosure.

FIG. 8 is a view illustrating a system for measuring an adhesive state of a patch according to an embodiment of the disclosure.

Referring to FIG. 8, a system 800 may include an output device 200 and an electronic device 100.

The electronic device 100 may include an inspection unit 120 and a detection unit 130.

The output device 200 may be an device for outputting patch adherence information. Examples of the output device 200 may include at least one of a smart phone, a tablet PC, a mobile phone, a video phone, an electronic book reader, a desktop PC, a laptop PC, a netbook computer, a PDA, a portable multimedia player (PMP), a MP3 player, a camera, or a wearable device. The wearable device may include at least one of an accessory type device such as a watch, a ring, a bracelet, a bracelet, a necklace, a pair of glasses, a contact lens or a head-mounted-device (HMD), a fabric or a garment all-in-one (e.g., digital clothing), a body attachment type (e.g., a skin pad or a tattoo), or a bio-implantable circuit. In some embodiments, examples of the output device 200 may be, at least one of, for example, a television, a digital video disk (DVD) player, an audio, a refrigerator, an air conditioner, a vacuum cleaner, an oven, a microwave oven, a washing machine, a set-top box, a home automation control panel, a security control panel, a media box (e.g., Samsung HomeSync™, Apple TV™, or Google TV™), a game console (e.g., Xbox™, and PlayStation™), an electronic dictionary, an electronic key, a camcorder, or an electronic frame. In other embodiments, the output device 200 may be configured to provide a variety of medical devices (e.g., various portable medical measurement devices such as blood glucose meters, heart rate meters, blood pressure meters, or temperature meters), magnetic resonance angiography (MRA), magnetic resonance imaging (MRI), computed tomography (CT), an imaging device, or an ultrasonic device), an Internet of thins, or a projector, but is not limited to the above-described devices.

Referring to FIG. 8, the output device 200 may include a controller 210, an output unit 220, and a communicator 230. The communicator 230 may perform communication with the electronic device 100. For example, the communication unit 230 may perform communication with the electronic device 100 using a communication network. The communication network may be, for example, an LTE, an LTE Advance (LTE-A), a code division multiple access (CDMA), a wideband CDMA (WCDMA), a universal mobile telecommunications system (UMTS), a wireless broadband (WiBro), Global System for Mobile Communications (GSM), or the like. According to another embodiment, the communication network may be, for example, wireless fidelity (WiFi), Bluetooth, Bluetooth low power (BLE), Zigbee, near field communication (NFC), Magnetic Secure Transmission, radio frequency (RF), or a body area network (BAN).

The output device 200 may control the output unit 220 to output skin measurement information (e.g., patch adherence information or detection result) received through a communicator 230. Examples of the output unit 220 may include, for example, a display (not shown), a speaker (not shown), a vibration device (not shown) or a light emitting device (not shown).

The electronic device 100 may consist of a control module 101 and a sensor module 102.

The control module 101 may include a controller 110, a communicator 113, a memory 114, a power source supplier 115, and a battery 116, and the sensor module 102 may include an irradiation unit 120 and a detection unit 130.

The irradiation unit 120 and the detection unit 130 of the sensor module 102 may correspond to the irradiation unit 120 and the detection unit 130 in FIG. 1, and thus the repeated description will be omitted.

The controller 110 may include a communication controller 111 and a sensor controller 112. The communicator controller 111 may establish communication connection between the electronic device 100 and the output device 200, and control to transmit data through the established channel by controlling the communicator 113. The sensor controller 1120 may control the sensor module 102, so that the irradiation unit 120 may irradiate light onto the skin, and the detection unit 130 in response to the irradiated light may detect a reflective light and convert light energy into electrical energy.

The communicator 113 may transmit the skin measurement information obtained by controlling the sensor controller 112 to the output device 200.

The memory 114 may store the acquired skin measurement information temporarily or permanently. In addition, the memory 114 may store an algorithm for calculating skin moisture level, melanin level, or erythema degree according to an algorithm for measuring skin and a detection result.

The power source supplier 115 may include a power management integrated circuit (PMIC), a charge IC, or the like as a power management module. The PMIC may have a wired and/or wireless charging scheme. The wireless charging scheme may include, for example, a magnetic resonance system, a magnetic induction system, or an electromagnetic wave system, and may further include an additional circuit for wireless charging, for example, a coil loop, a resonant circuit, a rectifier, etc. The battery 116 may include, for example, a rechargeable battery and/or a solar battery.

The controller 110 of the electronic device 100 may control the irradiation unit 120 to irradiate at least one light into the skin. For example, the irradiation unit 120 may irradiate at least one light into the skin to which the patch is adhered. The controller 110 of the electronic device 100 may control the detection unit 130 to detect the reflective light corresponding to the irradiation in the skin. For example, the detection unit 130 may detect the reflective light based on the amount of moisture in the skin changed by the physiologically active substances injected through the patch.

For an example embodiment, the controller 110 of the electronic device 100 may control the communicator 113 to transmit the detection intensity value of the reflective light to the output device 200. The output device 200 may receive the detection result through the communicator 230. The controller 210 of the output device 200 may identify the amount of moisture in the skin based on the detection intensity value of the reflective light. The output device 200 may generate patch adherence information indicating an adhesive state of a patch based on the identified amount of moisture. When the patch adherence information is generated, the output unit 220 of the output device 200 may output the generated patch adherence information. For example, when the output unit 220 includes a display, the output unit 220 may display visual information related to the patch adherence information on a display.

For another example, the controller 110 of the electronic device 100 may identify the amount of moisture in the skin based on the detection result of the reflective light. The controller 110 may control the communicator 113 to transmit the amount of moisture in the skin to the output device 200. The output device 200 may receive the amount of moisture in the skin though the communicator 230. The controller 210 of the output device 200 may generate the patch adherence information indicating the adhesive state of the patch in the skin based on the identified amount of moisture. When the patch adherence information is generated, the output unit 220 of the output device 200 may output the generated patch adherence information.

For another example, the controller 110 of the electronic device 100 may generate the patch adherence information indicating the skin adhesive state of the patch based on the detection result of the reflective light. The controller 110 may control the communicator 113 to transmit the patch adherence information to the output device 200. The communicator 230 of the output device 200 may receive the patch adherence information. The output unit 220 of the output device 200 may output the received patch adherence information.

For another example, the controller 110 of the electronic device 100 may generate the patch adherence information indicating the skin adhesive state of the patch based on the detection result of the reflective light. The controller 110 may provide the generated patch adherence information to the output unit (not shown). The output unit (not shown) may include, for example, a display (not shown), a speaker (not shown), a vibration device (not shown), and a light emitting device (not shown).

For various example embodiment, the controller 110 of the electronic device 100 may identify the amount of moisture in the skin to which the patch is adhered based on the detection result, and generate the patch adherence information indicating the skin adhesive state of the patch based on the identified amount of moisture.

According to various example embodiments, the patch adherence information may include information indicating that an entire patch is adhered to the skin when the identified amount of moisture is a value within a first range, information indicating that a part of patch is adhered to the skin when the identified amount of moisture is a value within a second range, and information indicating that the patch is not adhered to the skin when the identified amount of moisture is a value within a third range.

The values within the first range, the second range, and the third range may depend on the degree of moisture in the skin before the patch is adhered.

The irradiation unit 120 of the electronic device 100 may irradiate a plurality of lights into the skin, and the plurality of lights may include a reference light having a smaller reflectivity with respect to the change of an object to be measured, and a measurement light having a greater reflectivity with respect to the change of the object to be measured.

The detection unit 130 of the electronic device 100 may detect the first reflective light corresponding to the reference light and the second reflective light corresponding to the measurement light.

The detection result of at least one reflective light may include the intensity of the first reflective light and the intensity of the second reflective light.

The controller 110 of the electronic device 100 may set at least one of the irradiation time of at least one irradiated light, the irradiation intensity, and the detection time of at least one reflective light.

Figure 9:
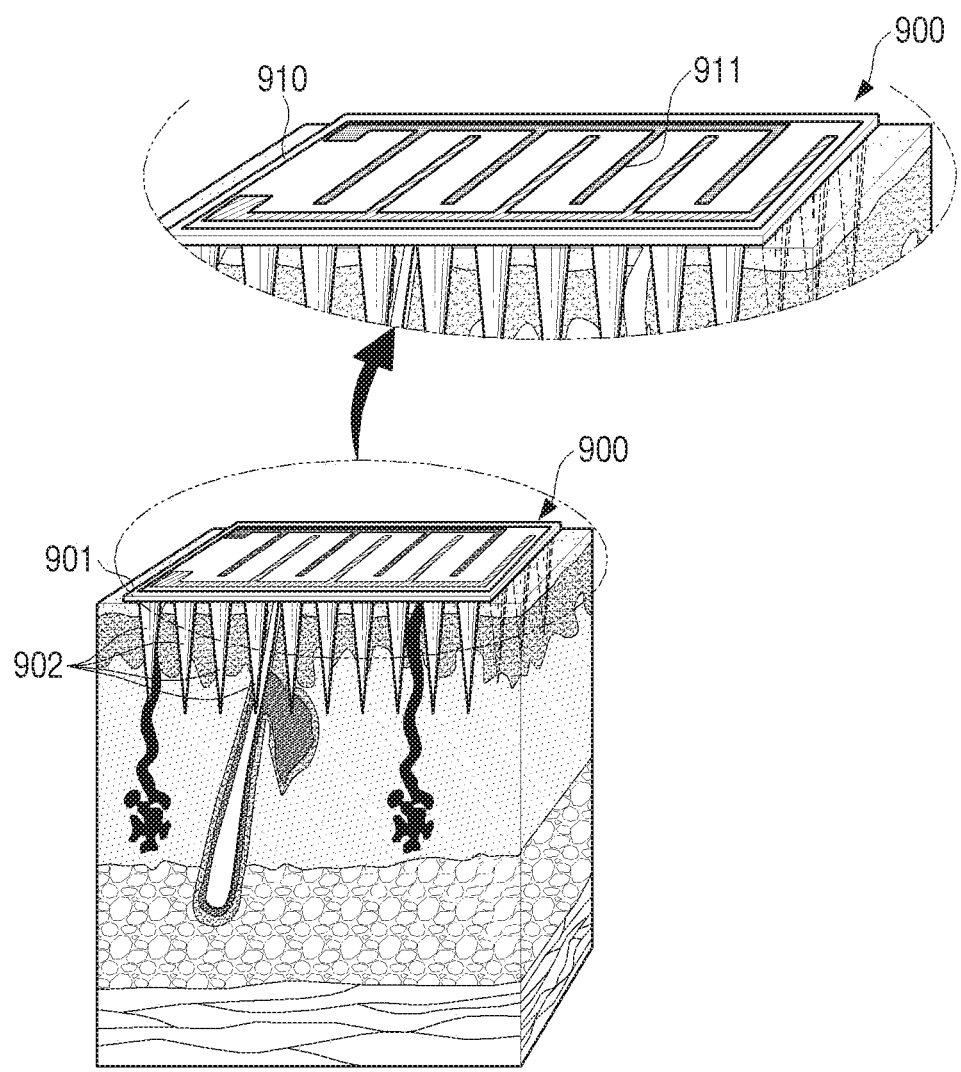
FIG. 9 is a view illustrating a micro needle patch on which an electronic device is mounted according to another embodiment of the disclosure.

FIG. 9 is a view illustrating a micro needle patch 900 on which an electronic device is mounted according to another embodiment of the disclosure.

Referring to FIG. 9, a micro needle patch 900 may include a support 901, micro needles 902 and an electronic device 910.

Referring to FIG. 9, the description of the support 901 and the micro-needles 902 corresponds to the description of the support 501 and the micro needles 602 in FIG. 6. Therefore, the repeated description will be omitted.

The electronic device 910 may formed on the surface of the support 901.

The electronic device 910 may include a controller (not shown) and an electrode sensor 911. The electrode sensor 911 may include, for example, an interdigitated electrode or an interdigitated electrode arrangement circuit.

The controller (not shown) may sense a capacitive between the micro needle patch 900 and the skin boundary surface by using a capacitive sensor. For example, when an interdigitated electrode is used, the controller (not shown) may sense the capacitive based on the frequency response or the change of a RC circuit according to an interdigitated electrode.

As the micro-needle patch 900 is closely adhered to the skin, an air layer in the micro-needle patch 900 and the skin may be gradually reduced. Accordingly, a permittivity on the skin boundary surface may be increased, and the capacitive may be detected to be great. However, as the micro needle patch 900 is distant from the skin, the air layer in the micro needle patch 900 and the skin may be increased. Therefore, the permittivity on the skin boundary surface may be reduced, and the capacitive may be detected to be small.

The controller (not shown) may generate the patch adherence information indicating the extent to which the patch is adhered to the skin based on the sensed capacitive value.

For example, when the sensed capacitive value is relatively great, the controller (not shown) may generate the patch adherence information including the information indicating that the patch is closely adhered. When the capacitive value is relatively small, the controller (not shown) may generate the patch adherence information including the information indicating that the patch is partially adhered. When the capacitive value is far smaller, the controller (not shown) may generate the patch adherence information including the information indicating that the patch is not adhered.

Figure 10:
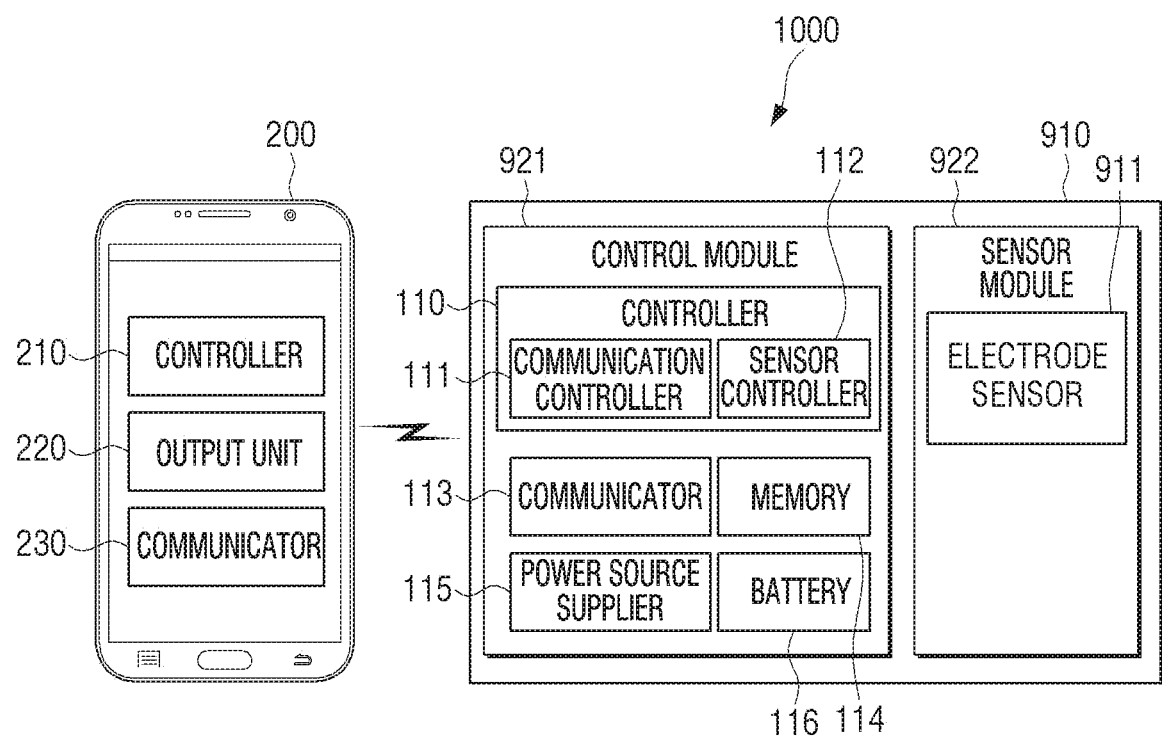
FIG. 10 is a view illustrating a system for measuring an adhesive state of a patch according to another embodiment of the disclosure.

FIG. 10 is a view illustrating a system 1000 for measuring an adhesive state of a patch according to another embodiment of the disclosure.

Referring to FIG. 10, a system 1000 may include an output device 200 and an electronic device 910.

The output device 200 may be one of the types of output device 200 in FIG. 8, and the electronic device 100 may include an electrode sensor 911 as shown in FIG. 9.

Referring to FIG. 10, an electronic device 200 may include a controller 210, an output unit 220, and a communicator 230.

The controller 210, the output unit 220 and the communicator 230 of the electronic device of FIG. 10 correspond to the controller 210, the output unit 220 and the communicator of FIG. 8, and thus the repeated description will be omitted.

The electronic device 910 may include a control module 921 and a sensor module 922.

The control module 921 of the electronic device 910 in FIG. 10 corresponds to the control module 101 of the electronic device 100 in FIG. 8, and thus the repeated description will be omitted.

The controller 110 of the electronic device 910 may control the electrode sensor 911 to sense the capacitive between skin boundary surface and the micro needle patch 900.

The controller 110 of the electronic device 910 may control the communicator 113 so that the sensed capacitive intensity value to the output device 200. The output device 200 may receive the detection result through the communicator 230. The controller 210 of the output device 200 may identify the degree of moisture in the skin based on the intensity value of the capacitive. The output device 200 may generate patch adherence information indicating the skin adhesive state of the patch based on the identified moisture degree. When the patch adherence information is generated, the output unit 220 of the output device 200 may output the generated patch adherence information.

For example, the controller 110 of the electronic device 910 may identify the degree of moisture in the skin based on the intensity value of the capacitive. The controller 110 may control the communicator 113 to transmit the degree of moisture in the skin to the output device 200. The output device 200 may receive the degree of moisture through the communicator 230. The controller 210 of the output device 200 may generate the patch adherence information indicating the skin adhesive state of the patch based on the identified degree of moisture. When the patch adherence information is generated, the output unit 220 of the output device 200 may output the generated patch adherence information.

The controller 110 of the electronic device 910 may identify the degree of moisture in the skin based on the intensity value of the capacitive, and generate the patch adherence information indicating the skin adhesive state of the patch based on the identified degree of moisture. The controller 110 may control the communicator 113 so that the patch adherence information may be transmitted to the output device 200. The communicator 230 of the output device 200 may receive the patch adherence information. The output unit 220 of the output device 200 may output the received patch adherence information.

Figure 11:
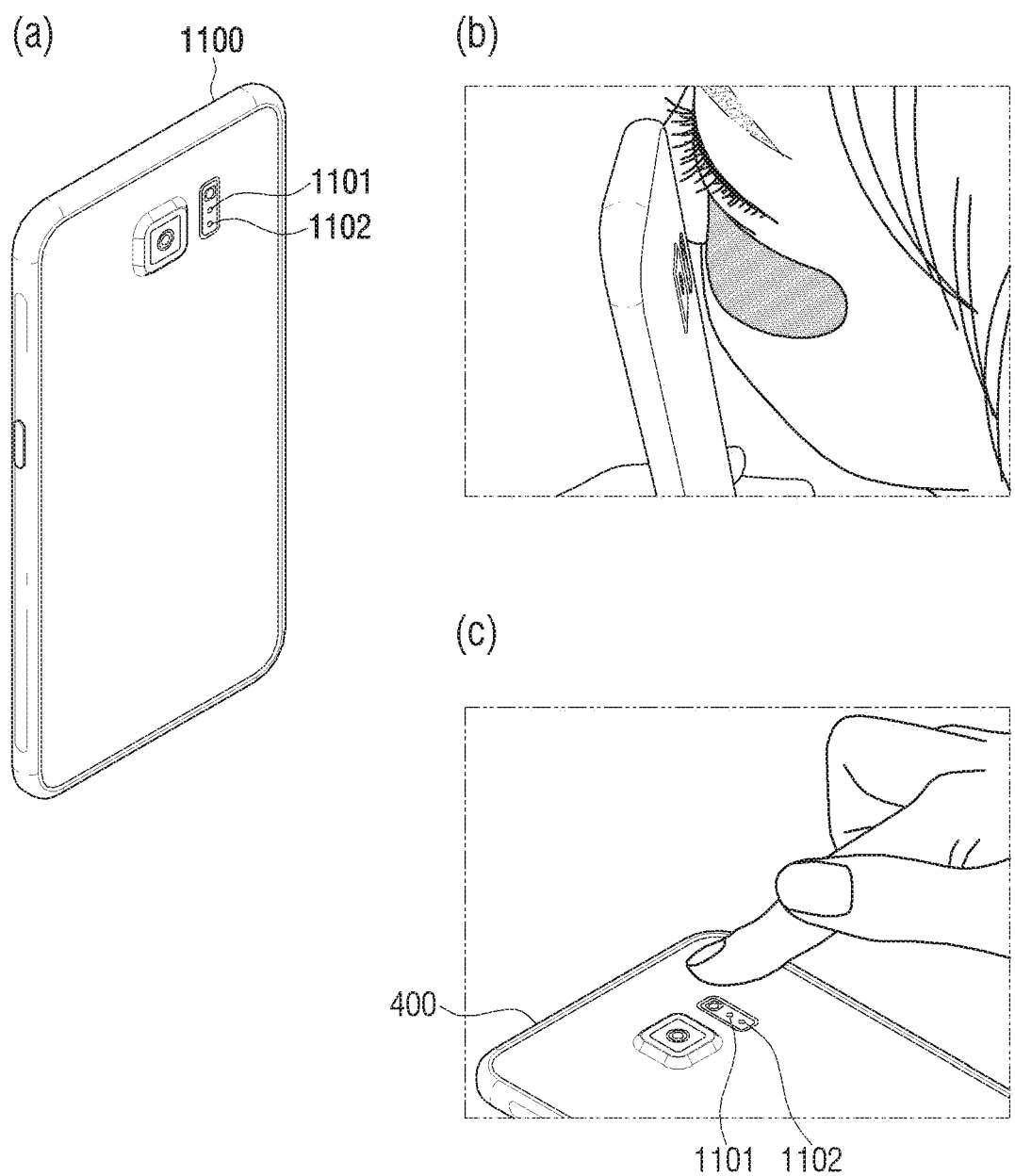
FIG. 11 is a view illustrating a portable device on which an electronic device is mounted according to an embodiment of the disclosure.

FIG. 11 is a view illustrating a portable device 1000 on which an electronic device 100 is mounted according to an embodiment of the disclosure.

The electronic device 100 may be part of the portable device 1100.

In FIG. 11, the portable device 1100 may be a smartphone, a tablet personal computer (a table PC), a mobile phone, a video phone, an e-book reader, a laptop PC laptop personal computer (a lap top PC), a netbook computer, a personal digital assistant (PDA), a portable multimedia player (PMP), an MP3 player, a mobile medical device, a camera, internet of things or a wearable device, or they may be part of them. A wearable device may be an accessory type device such as a watch, a ring, a bracelet, a bracelet, a necklace, a pair of glasses, a contact lens or a head-mounted-device (HMD), a fabric or a garment-all-in-one, a body attachment type (e.g., a skin pad or a tattoo), or a bio-implantable circuit.

The portable device 1100 shown in FIG. 11 (a) may include an irradiation unit 120 capable of irradiating at least one light into the skin having the patch adhered thereto and a detection unit 130 for detecting at least one reflected light reflected based on the amount of moisture in the skin. In this case, the irradiation unit 120 may include an LED that emits a reference light having a wavelength of 1450 nm and an LED that emits a measurement light having a wavelength of 880 nm. The detection unit 130 may include a PD capable of detecting a wavelength of 1450 nm and an LED capable of detecting a measurement light having a wavelength of 880 nm as the first reflected light corresponding to the reference light. The LED and the PD for irradiating and detecting light at the same wavelength may consist of one module. For example, an LED for irradiating light at a wavelength of 1450 nm and a PD for detecting light at a wavelength of 1450 mm may be implemented as one first module 1101. Alternatively, an LED for irradiating light a wavelength of 880 nm and a PD for detecting light at a wavelength of 880 nm may be embodied as one second module 1102.

Referring to FIG. 11 (b), a user may identify the degree of moisture in the skin to which the patch is adhered or the patch adhesive state by using the portable device 1100. The user may irradiate at least one light into the skin to which the patch is adhered by using the first module 1101 and the second module 1102 of the portable device 1100, and identify the degree of moisture in the skin to which the patch is adhered and the patch adhesive state based on the detection result of the reflective light corresponding to the irradiated light.

The portable device 1100 may irradiate at least one light into the skin to which the patch is adhered, and identify the degree of moisture in the skin based on the detection result of the reflective light corresponding to the irradiated light.

The portable device 1100 may generate the patch adherence information indicating the adhesive state of the patch based on the identified degree of moisture.

The portable device 1100 may provide the generated patch adherence information to the output unit (not shown) or the communicator (not shown). When the output unit (not shown) includes a display, the portable device 1100 may display visual information related to the patch adherence information on a screen through a display (not shown).

When the output unit (not shown) includes a speaker, the portable device 1100 may output auditory information related to the patch adherence information through the speaker.

According to various embodiments, at least one of the first module 1101 and the second module 1102 may also be used as a module used for pulse measurement of a user.

For pulse measurement, for example, LEDs and PDs for irradiating and detecting wavelengths of 530 nm, 660 nm, 880 mm and 940 nm may be used.

Referring to FIG. 11 (c), a user' pulse may be measured by using the portable device 1100.

Referring to FIG. 11, the portable device 1100 may not only identify the degree of moisture in the skin based on the detected reflective light, but also identify the pulse rate in the skin.

Figure 12:
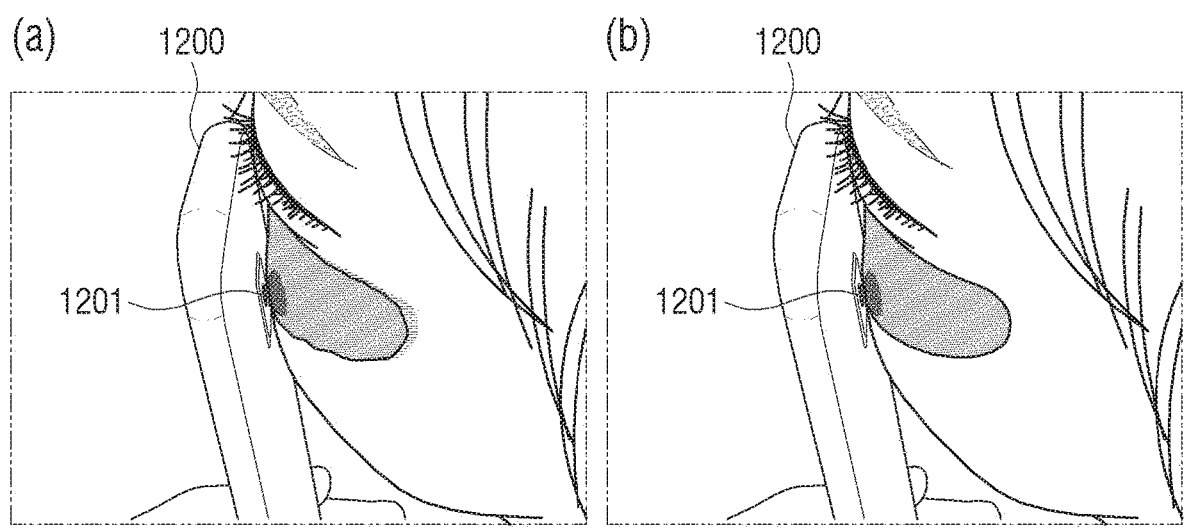
FIG. 12 is a view illustrating a portable device for measuring an adhesive state of a patch according to another embodiment of the disclosure.

FIG. 12 is a view illustrating a portable device 1200 for measuring an adhesive state of a patch according to another embodiment of the disclosure.

Referring to FIG. 12, the portable device 1200 may include a camera 1201 for capturing the outside.

The user may capture the patch adhered to the skin by using the camera 1201.

For example, (a) of FIG. 12 is a patch image captured when a part of the patch is adhered, and (b) of FIG. 12 is a patch image captured when an entire patch is adhered.

The portable device 1200 may identify an adhesive state of the patch to the skin by performing an image process on the captured patch image.

While capturing a patch image, the portable device 1200 may irradiate at least one light onto the skin to which the patch is adhered, and detect at least one reflective light based on the amount of moisture in the skin in response to the irradiated light.

The portable device 1200 may generate the patch adherence information indicating the adhesive state of the patch considering the image processed patch image and the detected reflective light.

For example, when it is set that both the image processed patch image and the detected reflective light are adhered to the entire patch, the portable device 1200 may generate the patch adherence information including the information indicating that the patch is firmly adhered.

When both the image processed patch image and the detected reflective light are determined to be only partially adhered, the portable device 1200 may generate patch adherence information including information indicating that only a part of the patch is adhered.

Figure 13:
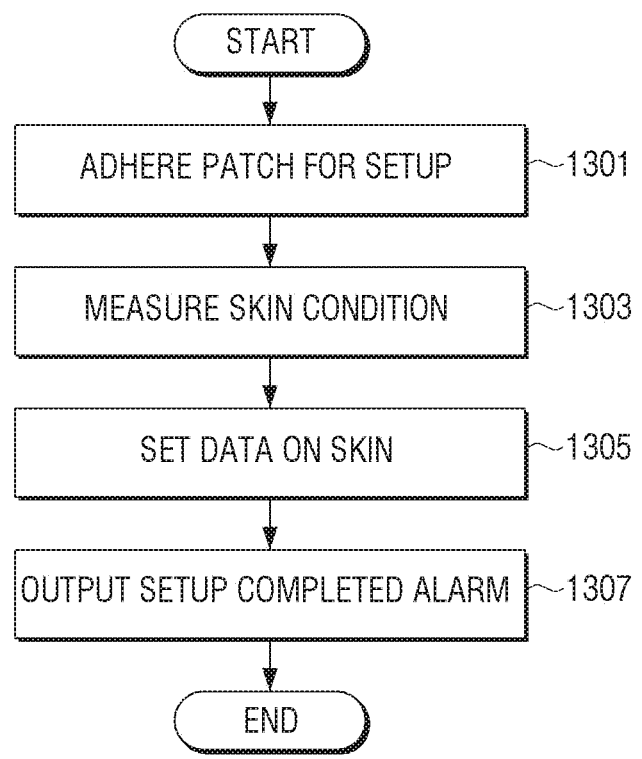
FIG. 13 is a flowchart to explain a process of measuring skin condition of an electronic device according to an embodiment of the disclosure.
Figure 14:
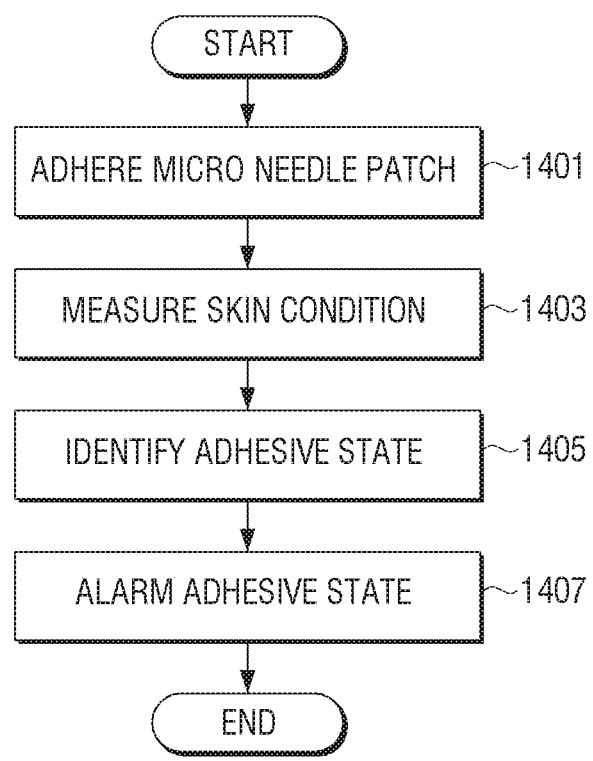
FIG. 14 is a flowchart to explain a process of measuring skin condition of an electronic device according to an embodiment of the disclosure.

FIG. 13 is a flowchart to explain a process of measuring skin condition of an electronic device 100 according to an embodiment of the disclosure, and FIG. 14 is a flowchart to explain a process of measuring skin condition of an electronic device 100 according to an embodiment of the disclosure.

When generating patch adherence information considering the degree of moisture, and if the same reference is applied to a user, the results may be different depending on the user' skin condition.

For example, when a user has skin of a high moisture level, (e.g., a user with oily skin), even if a litter part of micro needles is injected into the skin, the electronic device 100 may identify that the patch is firmly adhered. When a user has the skin of a low moisture level (e.g., a user with a dry skin), the electronic device 100 may identify that only the part of the patch is adhered to the skin even if all of the micro needles are injected into the skin.

Therefore, it is required to adjust the moisture range for generating patch adherence information considering the degree of moisture in the skin of the user before the patch is adhered.

FIG. 13 is a flowchart to explain a process of measuring skin condition of an electronic device according to an embodiment of the disclosure, and FIG. 14 is a flowchart to explain a process of measuring skin condition of an electronic device according to an embodiment of the disclosure.

At operation 1301, a user may adhere a patch for setting. The patch for setting may be a patch including an electronic device 100 without micro-needles.

At operation 1303, the patch for setting may measure the skin condition of a user (e.g., the degree of moisture of the skin).

The irradiation unit 120 of the electronic device 100 provided on the patch for setting may irradiate at least one light into the skin, and the detection unit 130 of the electronic device 100 may detect at least one reflective light based on the amount of moisture in the skin in response to at least one irradiated light.

The electronic device 100 may identify the amount of moisture in the skin based on the detection result.

When the amount of moisture is identified, at operation 1305, the electronic device 100 may set the data on the user's skin based on the identified moisture level.

For example, the electronic device 100 may set the moisture level for generating the patch adherence information. In other words, the electronic device 100 may set values within the first range to the third range used for generating the patch adherence information depending on the initial moisture level of the user's skin.

For example, when the moisture level of the skin is high, the electronic device 100 may set the value in the first range to be high.

To be specific, if the first range is between 70% to 95% as a default range, and patch adherence information including information indicating that the patch is firmly adhered is generated, when the moisture level of the skin is determined as being high, the electronic device 100 may set to generate the patch adherence information when the first range is between 80% and 95%.

For example, when the moisture level of the skin is high, the electronic device 100 may set the value in the first range to be high.

For example, when the moisture level of the skin is low, the electronic device 100 may set the value in the first range to be low.

To be specific, if the first range is between 70% to 95% as a default range, and patch adherence information including information indicating that the patch is firmly adhered is generated, when the moisture level of the skin is determined as being low, the electronic device 100 may set to generate the patch adherence information when the first range is between 60% and 95%.

The electronic device 100 may set the values in the first range to the third range differently considering the skin condition of the user.

When the setting of the data on the user's skin is completed, at operation 1307, the electronic device 100 may output alarming information indicating that the setting is completed.

For example, the electronic device 100 may output visual information indicating completed setup through a display or a light emitting unit or output auditory information through a speaker of the electronic device 100.

The electronic device 100 may transmit the completed setup data indicating that the setting has been completed to the output device 200 in communication connection with the electronic device 100. Based on the received completed setup data, the output device 200 may output visual information or sound information indicating the completed setup through the display or the speaker of the output device 200.

When the setting of the data on the user's skin is not completed, the electronic device 100 may output alarming information requesting re-measurement of the skin condition.

For example, the electronic device 100 may output the alarming information as visual information or auditory information. The electronic device 100 may transmit the re-measurement request data that requests the re-measurement to the output device 200 in communication connection with the electronic device 100. The output device 200 may output visual information and auditory information that requests re-measurement based on the received re-measurement request data.

When the data on the user' skin is set, at operation 1401 of FIG. 14, a user may adhere the micro-needle patch 600 on which the electronic device 100 is mounted.

At operation 1403, the micro needle patch 600 may measure the skin condition of the user (e.g., the moisture level).

The irradiation unit 120 of the electronic device 100 provided in the micro-needle patch 600 may irradiate at least one light into the skin, and the detection unit 130 of the electronic device 100 may detect at least one reflective light based on the moisture level of the skin in response to the at least one irradiated light.

The electronic device 100 may identify the moisture level of the skin based on the detection result.

At operation 1405, the electronic device 100 may identity the adhesive state of the patch based on the data on the skin set in FIG. 13.

For example, when the moisture level is a value in the first range set in FIG. 13, the electronic device 100 may include information indicating that the entire patch is adhered to the skin, when the moisture level is a value in the first range set in FIG. 13, the electronic device 100 may include information indicating that the entire patch is adhered to the skin, when the moisture level is a value in the second range set in FIG. 13, the electronic device 100 may include information indicating that a part of the patch is adhered to the skin, and when the moisture level is a value in the third range set in FIG. 13, the electronic device 100 may include information indicating that the patch is not adhered to the skin.

At operation 1407, the electronic device 100 may notify the adhesive state of the patch.

For example, when the patch adherence information indicating the adhesive state of the patch is generated based on the moisture level, the electronic device 100 may provide the generated patch adherence information to the output unit or the communicator.

When a display or a speaker is provided in the electronic device 100, the electronic device 100 may output patch adherence information as visual information through a display, or output the patch adherence information as sound information through a speaker. When the electronic device 100 provides the patch adherence information to the communicator, the output device 200 that receives the patch adherence information may output the patch adherence information as the visual information through the display, or output the patch adherence information as sound information through the speaker.

Figure 15:
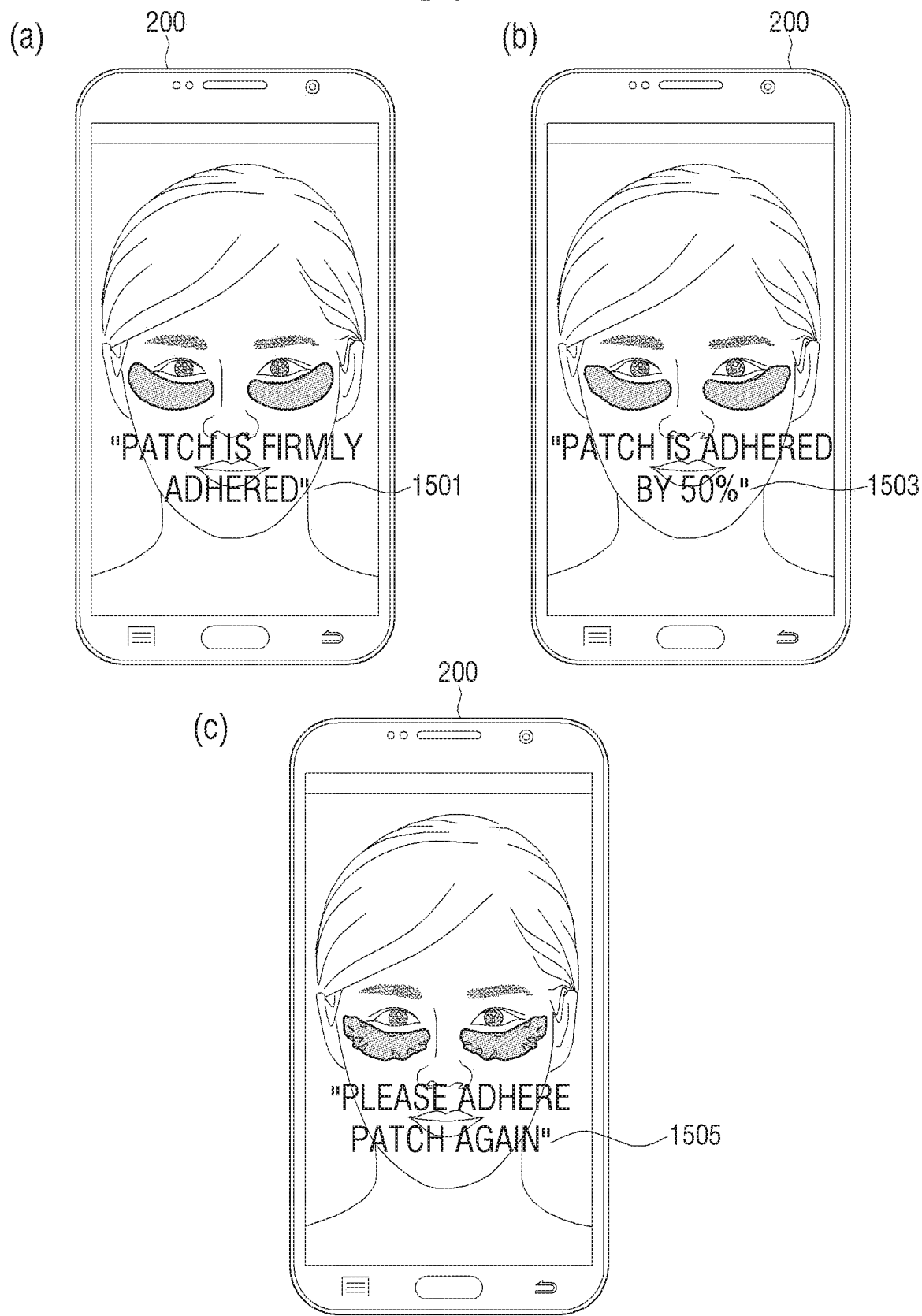
FIG. 15 is a view illustrating an output device for displaying visual information relating to patch adherence information on a screen according to an embodiment of the disclosure.

FIG. 15 is a view illustrating an output device 200 for displaying visual information relating to patch adherence information on a screen according to an embodiment of the disclosure.

When the electronic device 100 obtains the detection result in the skin (e.g., a detection intensity value of the reflective light or a capacitive value of a skin boundary surface, etc.), the electronic device 100 may transmit the detection result to the output device. The electronic device 100 may transmit the skin condition information (e.g., the moisture level in the skin) identified based on the detection result to the output device 200. The electronic device 100 may transit the patch adherence information generated based on the skin condition to the output device 200.

The output device 200 may display the visual information relating to the patch adherence information based on at least one of the received detection result, the skin condition information or the patch adherence information as shown in FIG. 15.

For example, referring to (a) of FIG. 15, the electronic device 100 may display visual information indicating that the patch is closely adhered. The electronic device 100 may display text information 1501 indicating that the patch is firmly adhered on a screen.

Referring to FIG. 15 (*b*), the electronic device 100 may display visual information indicating that the patch is partially adhered. The electronic device 100 may display text information 1503 indicating that adhesive degree of the patch as a percentage value.

As another example, as shown in FIG. 15 (C), the electronic device 100 may display visual information indicating that the patch is not adhered or is hardly adhered. In this case, the electronic device 100 may display text information 1505 indicating the degree of adhesion of the patch or re-adhesion of the patch together with the screen.

Figure 16:
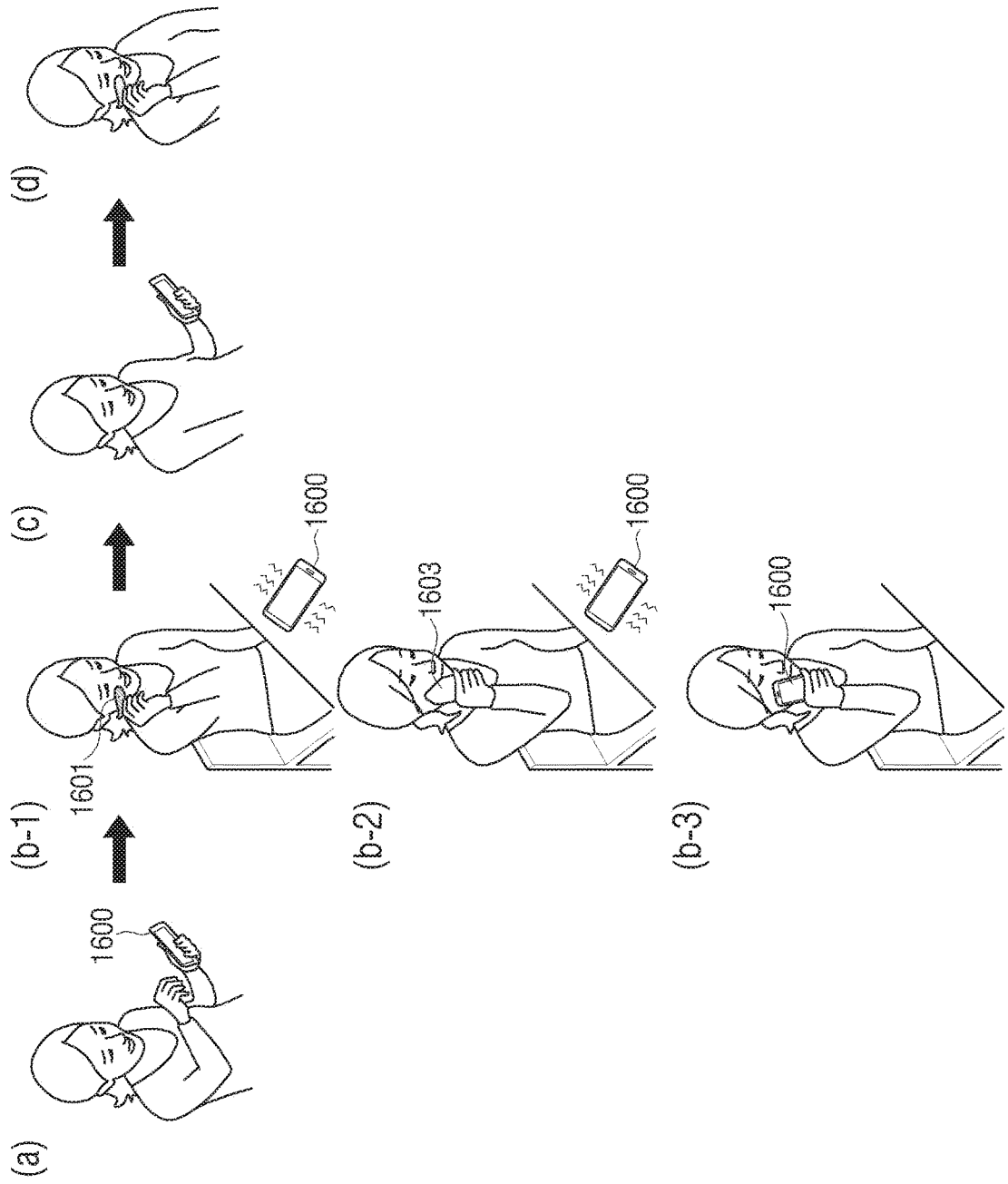
FIG. 16 is a usage view illustrating skin measurement and patch adherence information according to an embodiment of the disclosure.

FIG. 16 is a usage view illustrating skin measurement and patch adherence information according to an embodiment of the disclosure.

Referring to FIG. 16 (*a*), a user may execute an application for skin measurement by using a portable device 1600. The user may conduct a smart questionnaire on the skin by using the executed application.

Figure 17:
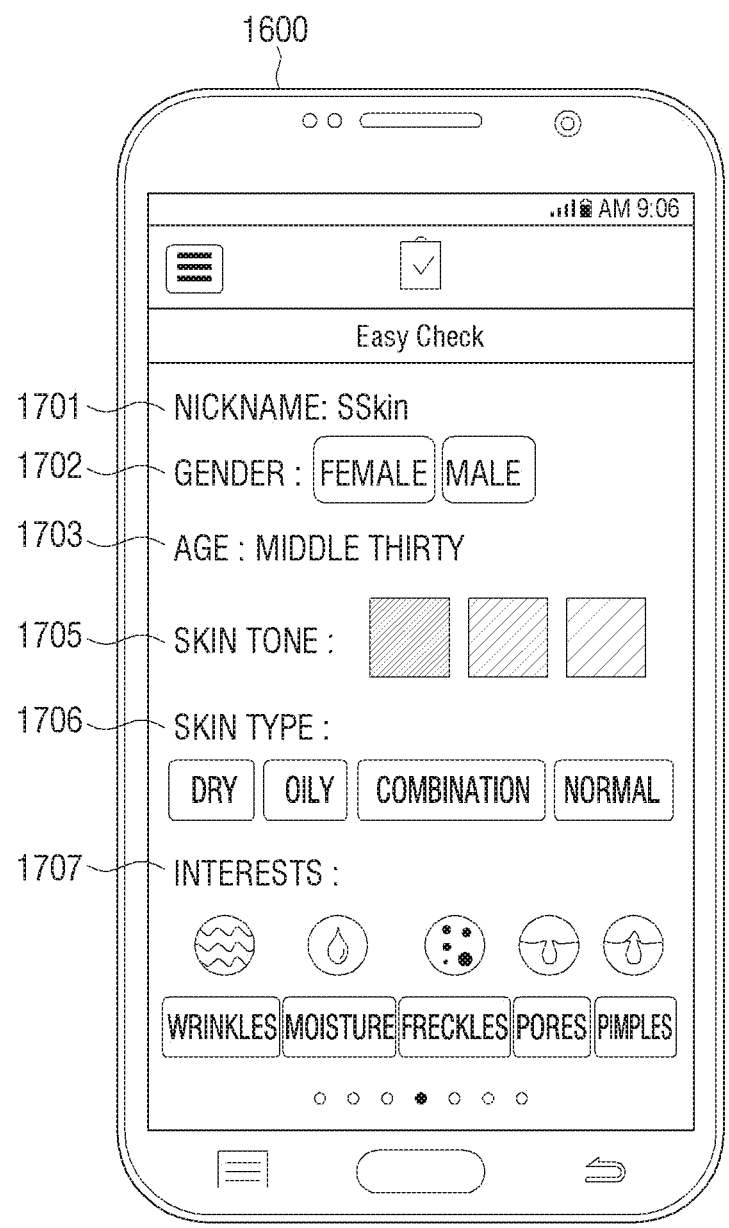
FIG. 17 is a view illustrating a smart questionnaire screen according to an embodiment of the disclosure.

Referring to FIG. 17, the portable device 1600 may display a smart questionnaire screen. The smart questionnaire screen may include, for example, at least one of a user name setting item 1701, a gender setting item 1702, an age setting item 1703, a skin tone setting item 1705, a skin type setting item 1706, and interest setting item, etc. 1707.

The user may input user's basic information and skin information by using the smart questionnaire screen.

The user may measure the skin condition of the user before the patch is adhered.

For example, referring to (b-1) of FIG. 16, in order to measure the skin condition, the user may, for example, use the patch for setting 1601 shown in FIG. 13. The detection result measured by using the patch for setting 1601 may be transmitted to the portable device 1600 of the user. The information on the user's skin condition identified based on the detection result may be transmitted to the portable device 1600.

Referring to (b-2) of FIG. 16, the user may user a skin measurement device 1603 for the user to measure the skin condition.

The skin measurement device 1603 may have a skin care function as well as a skin condition measurement function. The skin measurement device 1603 may have, for example, thermal, cold, ultrasonic, vibration, functions, and the like. In the case of a warming function, the skin measurement device 1603 may induce the activation of the user's pores, bloodstream, and lymphatics, thereby accelerating the injection of the physiologically active substance into the skin and the delivery into the blood vessel. In addition, in the case of a cold/hot function, the skin measurement device 1603 may provide effects such as skin elasticity, skin soothing, and pore reduction. In the case of an ultrasound function, the skin measurement device 1603 may irradiate an ultrasonic wave of 0.5 MHz to 5 MHz to raise the temperature of the local tissue to regenerate collagen, or to improve skin elasticity as a lifting effect.

The detection result measured by using the skin measurement device 1603 may be transmitted to the portable device 1600. The information on the skin condition identified based on the detection result may be transmitted to the portable device 1600.

Referring to (b-3) of FIG. 16, a user may directly use the portable device 1600 in order to measure the skin condition. The electronic device 100 in FIG. 1 may be mounted on the portable device 1600.

When the user's skin condition is measured, referring to (c) of FIG. 16, the user may identify the measurement result of the skin condition through the screen of the portable device 1600.

Figure 18:
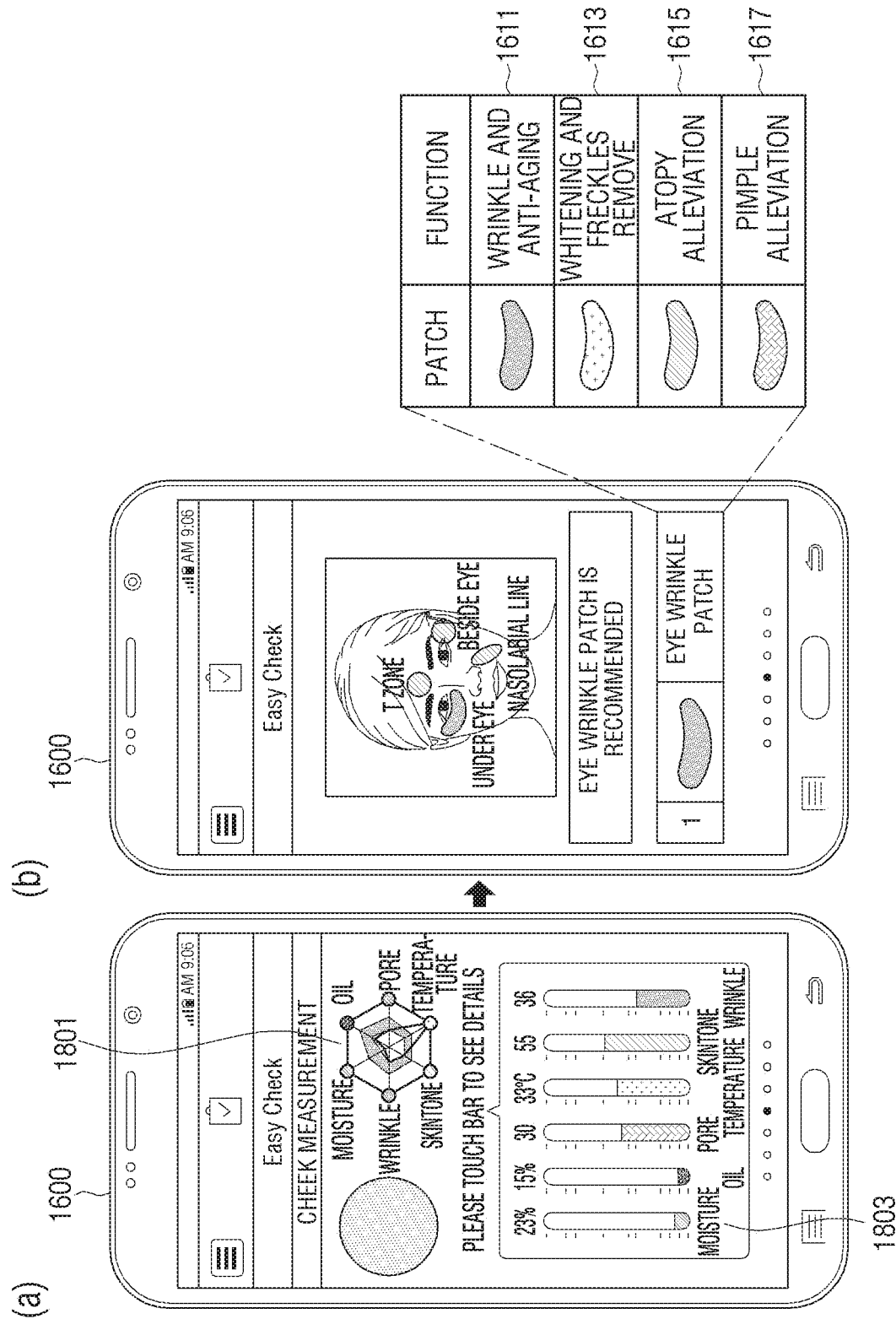
FIG. 18 is a view illustrating a screen for showing a skin condition measurement result and a customized patch according to an embodiment of the disclosure.

For example, referring to (a) of FIG. 18, a screen indicating the skin condition measurement result may be provided through the display of the portable device 1600. Referring to (a) of FIG. 18, information on the skin condition (e.g., moisture, oil, wrinkles, pores, temperature and skin tone, etc.) may be expressed by a radiation graph 1801 for comparing the reference amount with the measured amount.

Specific figures on information regarding the skin condition may be expressed by a bar graph 1803.

The screen for providing the measurement result of the skin condition as shown in (a) of FIG. 18 is a descriptive example, but the measurement result of the skin condition may be provided in the form of various interfaces and graphics.

Referring to (b) of FIG. 18, the portable device 1600 may recommend a user customized patch based on user's skin condition.

Referring to (b) of FIG. 18, the user-customized patch may include at least one of wrinkle and anti-aging patch 1611, a whitening and staining patch 1613, an atopy reducing patch 1615, and a pimple reducing patch 1615. However, these are merely examples, and customized patches may be provided for various uses or functions based on the skin condition of the user.

The user who has recommended the customized patch may adhere the recommended customized patch as shown in FIG. 16 (*d*).

Thus, customized care according to the skin condition of the user may become possible.

Figure 19:
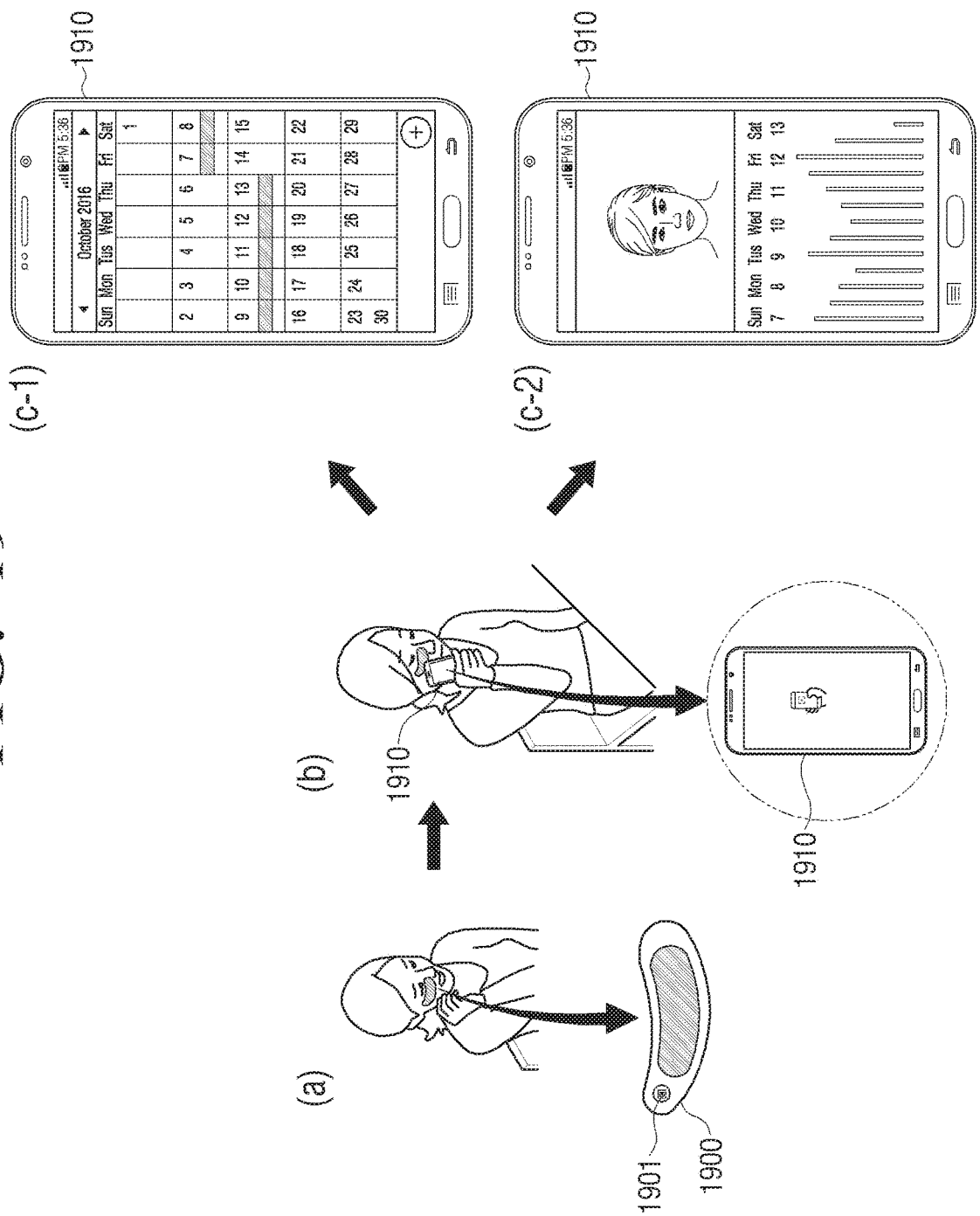
FIG. 19 is a usage view illustrating a process of managing a patch according to an embodiment of the disclosure.
Figure 20:
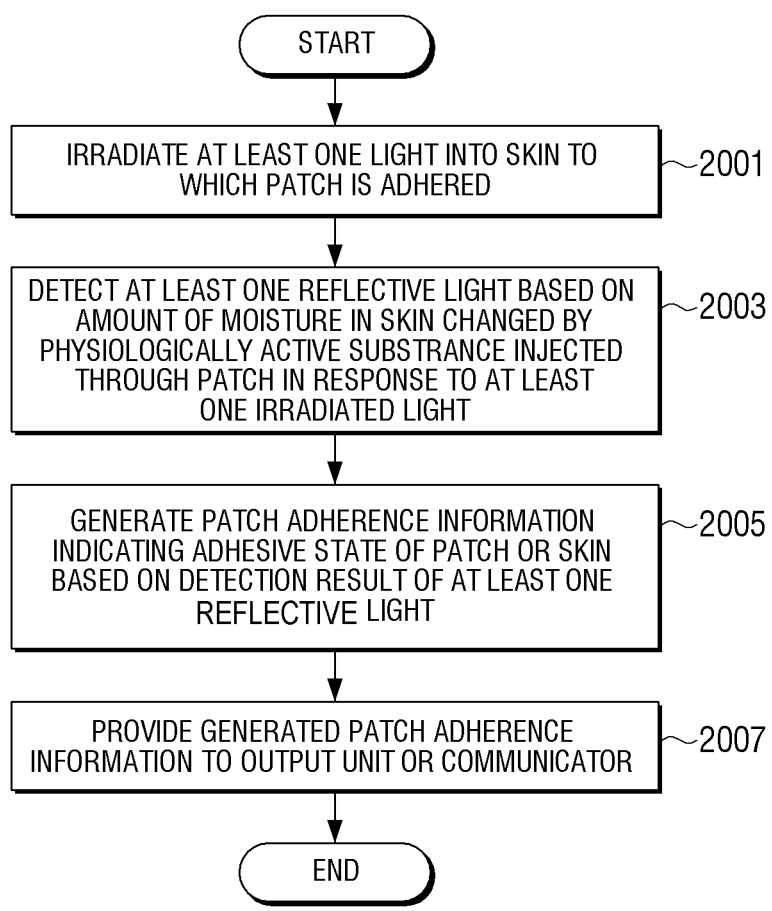
FIG. 20 is a flowchart to explain a method for measuring skin condition according to an embodiment of the disclosure.

FIG. 19 is a usage view illustrating a process of managing a patch according to an embodiment of the disclosure.

When a user adheres the recommended customized patch to the skin, the user may regularly manage the adhered patch.

For example, referring to (a) of FIG. 19, an electrical tag (e.g., an NFC tag or an RFID tag) 1901 may be included in the patch 1900. The electrical tag 1901 may be adhered to a surface of the support of the patch 1900, or printed on a support by a typical patterning process. The electrical tag 1901 may include information on the patch on which the electrical tag 1901 is provided. The information on the patch may be, for example, information on the patch type, the expiration date of the patch, or the manufacture of the patch.

Referring to (b) of FIG. 19, the user may execute a tag recognition application mounted on the portable device 1910, and tag a portable device 1910 to the electronic tag 1901 provided on the patch.

When the electronic tag 1901 is tagged, information on the patch included in the electronic tag 1901 of the patch 1900 may be transmitted to the portable device 1910. The portable device 1910 may recognize that the patch is adhered to the user's skin, and manage the adhered patch.

For another example, the user may directly tag a touch recognition module (not shown) provided on the support of the patch 1900 with fingers. The information on the patch may be transmitted to the portable device 1910. The information on the patch may be transmitted using a communication method of the electronic tag, and transmitted to the portable device 1910 through an additional near field communication module. The portable device 1910 that receives the information on the patch may recognize that the patch is adhered to the skin and manage the adhered patch. Information on a touch point of an electronic tag may be transmitted to the portable device 1910 along with the information on the patch.

According to various example embodiments, (a) and (b) of FIG. 19 show that the user tags an electronic tag after adhering a patch, but depending on the example of use, the user may tag the electronic tag provided on the patch first, and then adhere the patch.

The information on the patch may include the detection result of the skin condition (e.g., a detection intensity value of a reflective light or a capacitive value of a skin boundary surface, etc.), the skin condition information based on the detection result (e.g., a moisture level of the skin), or the patch adherence information generated based on the skin condition.

The portable device 1910 may manage the patch based on the information on the patch.

Referring to (c-1) of FIG. 19, the portable device 1910 may display ticks when to change or manage the patch on a calendar to regularly manage the patch. The calendar may be provided through an additional patch management application. The time point for changing or managing the patch may be shown as a new schedule of the calendar application pre-mounted on the portable device 1910.

The information on the skin condition which is registered on the adhered patch may be transmitted to the portable device 1910 regularly or when a user tags the patch. As shown in (c-2) of FIG. 19, at least one date or history information of the detection result of the skin condition, the skin condition information or the patch adherence information included in the information on the skin condition may be displayed on the screen.

As described above, customized patch recommendation and management may become possible based on the user skin condition, and user satisfaction may be enhanced.

According to various example embodiments, information on a new product (e.g., patches, cosmetic products, therapeutic products, or where to buy the products) according to the recommended patch and the patch management or a screen for purchasing the products may be further provided. In other words, the range of user experience may be significantly expanded from the use of the patch for measuring user skin condition to the purchasing service of a new product for skin care.

FIG. 19 is a usage view illustrating a process of managing a patch according to an embodiment of the disclosure.

At operation 2001, an electronic device 100 may irradiate at least one light into the skin to which the patch is adhered.

At operation 2003, the electronic device 100 may detect at least one reflective light based on the amount of moisture in the skin changed by the physiologically active substances injected through the patch in response to the at least one irradiated light.

At operation 2005, the electronic device 100 may generate the patch adherence information indicating the skin adhesive state of the patch based on the detection result of at least one reflective light.

Based on the detection result, the operation of generating the patch adherence information may include identifying the moisture level in the skin to which the patch is adhered, and generating the patch adherence information indicating the skin adhesive state of the patch based on the identified moisture level.

According to various example embodiments, irradiating of at least one light may include irradiating a plurality of light into the skin, and the plurality of light may include a reference light having a smaller reflectivity with respect to the change in the object to be measured, and a measurement light having a greater reflectivity with respect to the change in the object to be measured.

The detecting of at least one reflective light may include detecting a first reflective light corresponding to the reference light and a second reflective light corresponding to a measurement light.

The detection result of at least one reflective light may include the intensity of the first reflective light and the intensity of the second reflective light.

The electronic device 100 may set at least one of an irradiation time of at least one irradiation light, an irradiation intensity, and a detection time of the at least one reflective light.

At operation 2007, the electronic device 100 may provide the generated patch adherence information to an output unit or a communicator. When the output unit of the electronic device 100 includes a display, the electronic device 100 may control the display to display visual information related to the patch adherence information on a screen. The electronic device 100 may control the communicator to transmit the patch adherence information to an external device.

Figure 21:
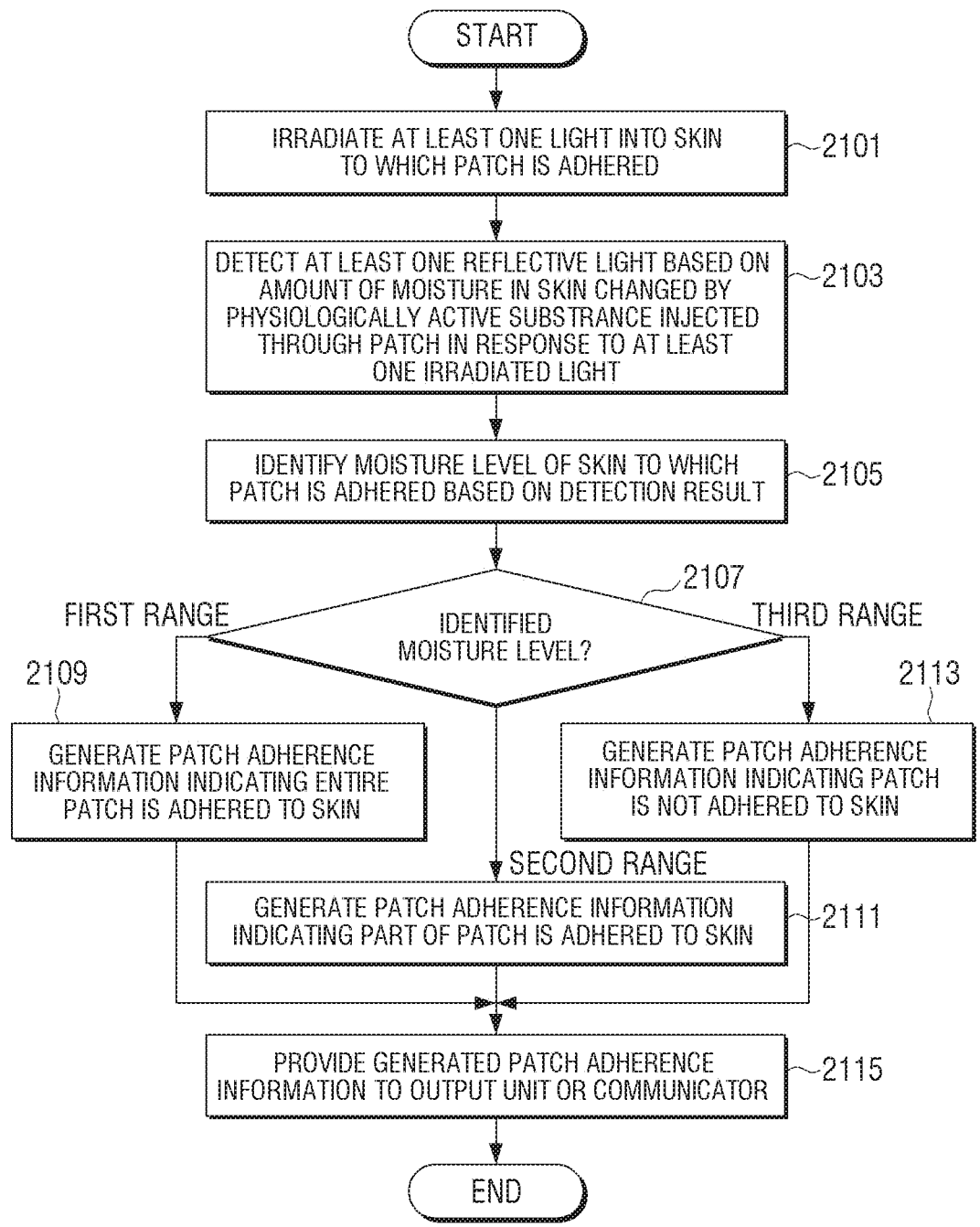
FIG. 21 is a flowchart to explain a method for measuring skin condition according to an embodiment of the disclosure.

FIG. 21 is a flowchart to explain a method for measuring a skin condition according to an embodiment of the disclosure.

At operation 2101, an electronic device 100 may irradiate at least one light into skin to which the patch is adhered.

At operation 2103, the electronic device 100 may detect at least one reflective light based on the moisture level of the skin changed by physiologically active substances injected through the patch in response to the at least one irradiated light.

At operation 2105, the electronic device 100 may identify the moisture level of the skin to which the patch is adhered based on the detection result of at least one reflective light.

At operation 2107, the electronic device 100 may identify whether the identified moisture level is within the first range, the second range or the third range.

When the value is within the first range, at operation 2109, the electronic device 100 may generate patch adherence information indicating that an entire patch is adhered to the skin.

When the value is within the second range, at operation 2111, the electronic device 100 may generate patch adherence information indicating that part of the patch is adhered to the skin.

When the value is within the third range, at operation 2113, the electronic device 100 may generate patch adherence information indicating that the patch is not adhered to the skin.

When the patch adherence information is generated, at operation 2115, the electronic device 100 may provide the generated patch adherence information to the output unit or the communicator.

Figure 22:
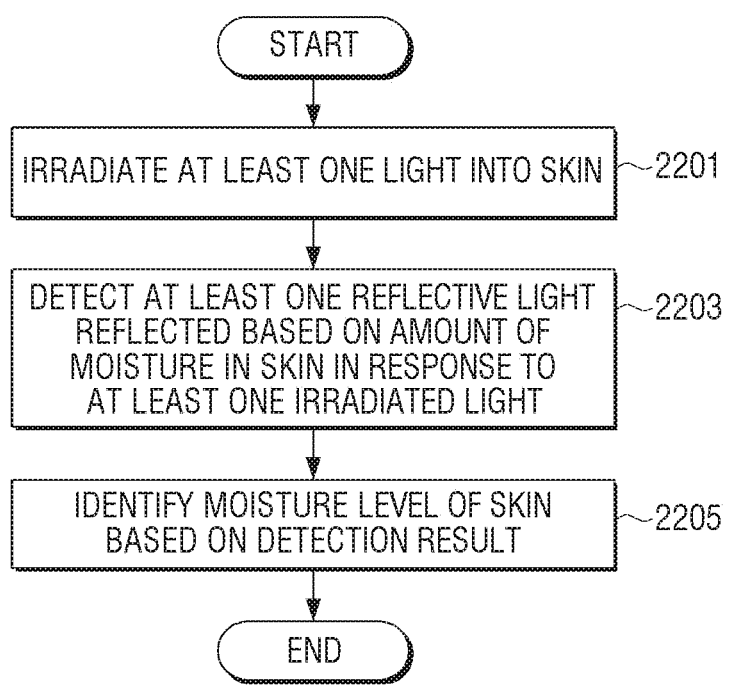
FIG. 22 is a flowchart to explain a method for measuring skin condition according to an embodiment of the disclosure.

FIG. 22 is a flowchart to explain a method for measuring a skin condition according to an embodiment of the disclosure.

At operation 2201, the electronic device 100 may irradiate at least one light into the skin.

At operation 2203, the electronic device 100 may detect at least one reflective light reflected based on the skin condition in response to at least one irradiated light.

At operation 2205, the electronic device 100 may identify the moisture level of the skin based on the detection result.

Figure 23:
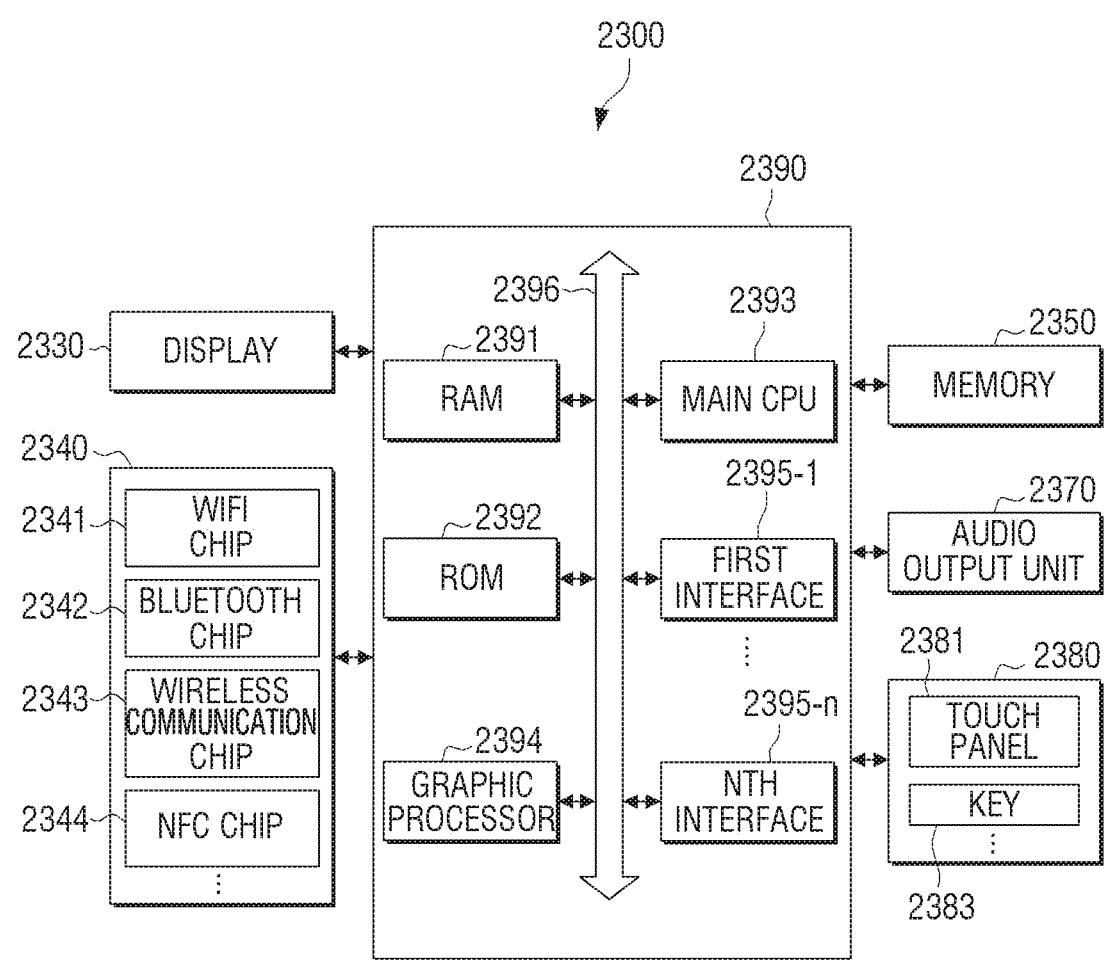
FIG. 23 is a block diagram illustrating configuration of an electronic device according to various embodiments of the disclosure.

FIG. 23 is a block diagram illustrating configuration of an electronic device 2300 according various embodiments of the disclosure.

An electronic device 2300 of FIG. 23 may be an example of the output device 100 of FIG. 8, an example of the portable device 1100 of FIG. 11, an example of the portable device 1200 of FIG. 12, an example of the portable device 1600 of FIG. 16, or an example of the portable device 1910 of FIG. 19.

Referring to FIG. 23, an electronic device 2330 may include at least one of a display 2330, a communicator 2340, a memory 2350, an audio output unit 2370, a user input unit 2380, and a processor 2390. However, the configuration of the electronic device shown in FIG. 23 is merely an example embodiment, but it is not limited thereto. Therefore, the part of the configuration of the electronic device 2300 shown in FIG. 23 may be omitted, modified, or added depending on the type of the electronic device 2300 or the purpose of the electronic device 2300.

The display 2330 may display visual information on a display area. The display 2330 may be engaged with at least one a front surface area, a side surface area, and a rear surface area of the electronic device 2300 in the form of a flexible display. The flexible display may be bent, curved or rolled without cracking through a thin and flexible substrate as thin as a piece of paper.

The display 2330 may be embodied with a touch screen in a layer structure in combination with a touch panel 2380. The touch screen may include a display function as well as a sensing function of a touch input position, a touch area and a touch input pressure. In addition, the touch screen may include sensing functions of not only a real-touch but also a proximity touch.

The communicator 2340 may perform communication with various types of external devices according to various types of communication methods. The communicator 2340 may include at least one of a Wi-Fi chip 2341, a Bluetooth chip 2342, a wireless communication chip 2343, and an NFC chip 2344. The processor 2390 may communicate with an external server or various external devices using the communicator 2340.

The memory 2350 may store various programs and data necessary for the operation of the electronic device 2300. The memory 2350 may be implemented with a non-volatile memory, a volatile memory, a flash memory, a hard disk drive (HDD), or a solid state drive (SSD). The memory 2350 may be accessed by the processor 250 and reading/writing/modifying/deleting/updating operations of data may be performed by the processor 2390. The term 'memory' in this disclosure may include the memory 2350, and a memory card (not shown) (e.g., a micro SD card, a memory stick, etc.) mounted in ROM (not shown), RAM (not shown) or the electronic device 2300 in the processor 2390.

The memory 2350 may store programs and data for forming various screens displayed on a display screen of the display 2330. The memory 2350 may store a data recognition model.

The audio output unit 2370 may output various alarming sounds or voice messages as well as various audio data. The audio output unit 2370 may be embodied as a speaker, but it is not limited thereto. The audio output unit 2370 may be embodied as an output terminal for outputting audio data.

The user input unit 2380 may receive various user inputs and transmit the various user inputs to the processor 2390. The user input unit 2380 may include, for example, a touch panel 2381 or a key 2383. The touch panel 2381 may use, for example, at least one of an electrostatic type, a pressure sensitive type, an infrared type, and an ultrasonic type. The touch panel 2381 may further include a control circuit. The touch panel 2381 may further include a tactile layer and provide touch reaction to a user. The key 2383 may include, for example, a physical button, an optical key, or a keypad.

The processor 2390 (or, a controller) may control the overall operation of the electronic device 2300 by using the various programs stored in the memory 2350.

The processor 2390 may include a RAM 2391, a ROM 2392, a graphics processor 2393, a main CPU 2394, first to nth interfaces 2395-1 to 2395-n, and a bus 2396. The RAM 2391, the ROM 2392, the graphics processor 2393, the main CPU 2394, the first to nth interfaces 2395-1 to 2395-n, etc. may be connected to one another via the bus 2396.

The constituent elements of the electronic device 2300 may be differently named. The electronic device 2300 may include at least one of the above-described constituent elements, and some constituent elements may be omitted or additional constituent elements may be further included. For example, the electronic device 2300 may further include an inspection unit 120 and a detection unit 130.

Figure 24:
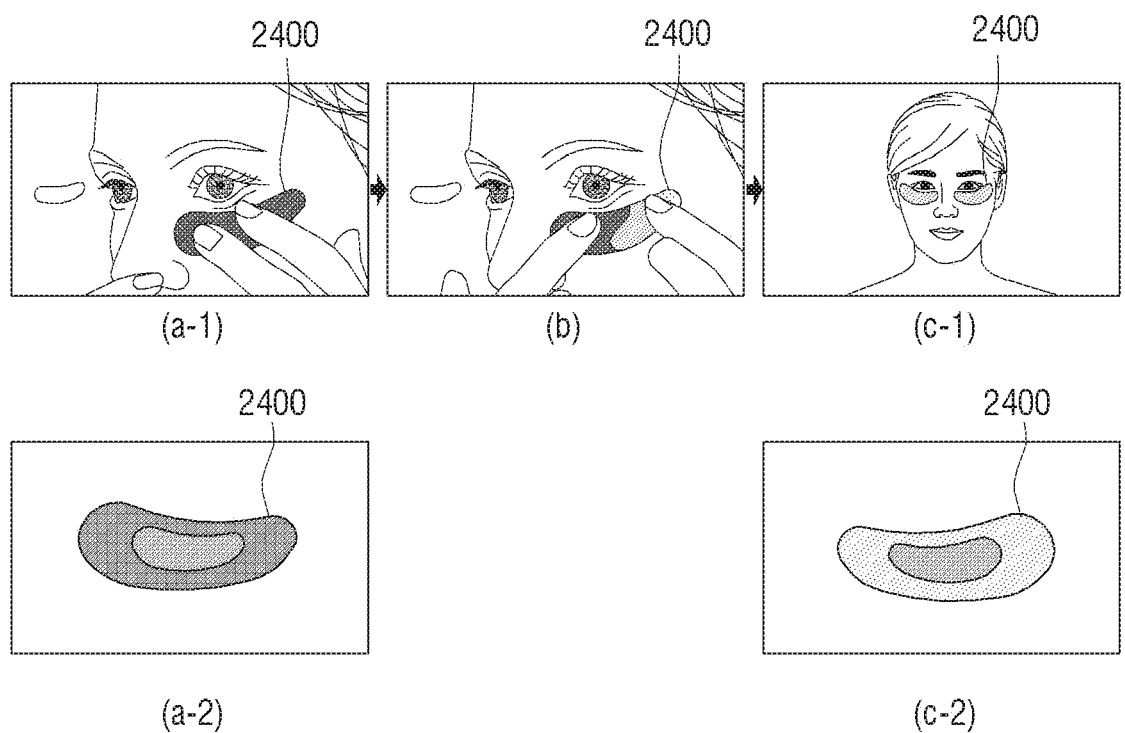
FIG. 24 is a usage view illustrating a process of adhering a patch according to an embodiment of the disclosure.

FIG. 24 is a usage view illustrating a process of adhering a patch according to an embodiment of the disclosure.

Referring to FIG. 24, a patch 2400 may be a patch that changes color depending on the temperature.

For example, in (a-1) of FIG. 24, the user may try to adhere a patch 2400 to the face. The color of the patch 2400 before adhered may be represented by the first color as shown in (a-2) of FIG. 24.

Referring to (b) of FIG. 24, the user may press the patch 2400 using a hand or a tool so as to be in close contact with the skin.

The portion of the patch 2400 adhering to the skin may change from the first color to the second color as the temperature increases due to conduction of the body temperature.

Referring to (c-1) of FIG. 24, when the entire patch 2400 is firmly adhered to the skin, the entire (or most) color of the patch 2400 after being adhered to the skin may be changed to the second color as shown in (c-2) of FIG. 24.

According to various embodiments, if the first color is colored, the second color may be colorless, skin color, or transparent color. Alternatively, if the first color is a high-brightness color, the second color may be a low-brightness color. Alternatively, if the first color is a high saturation color, the second color may be a low saturation color. Alternatively, the first color and the second color may be a color relationship in contrast with each other (e.g., complementary color).

Figure 25:
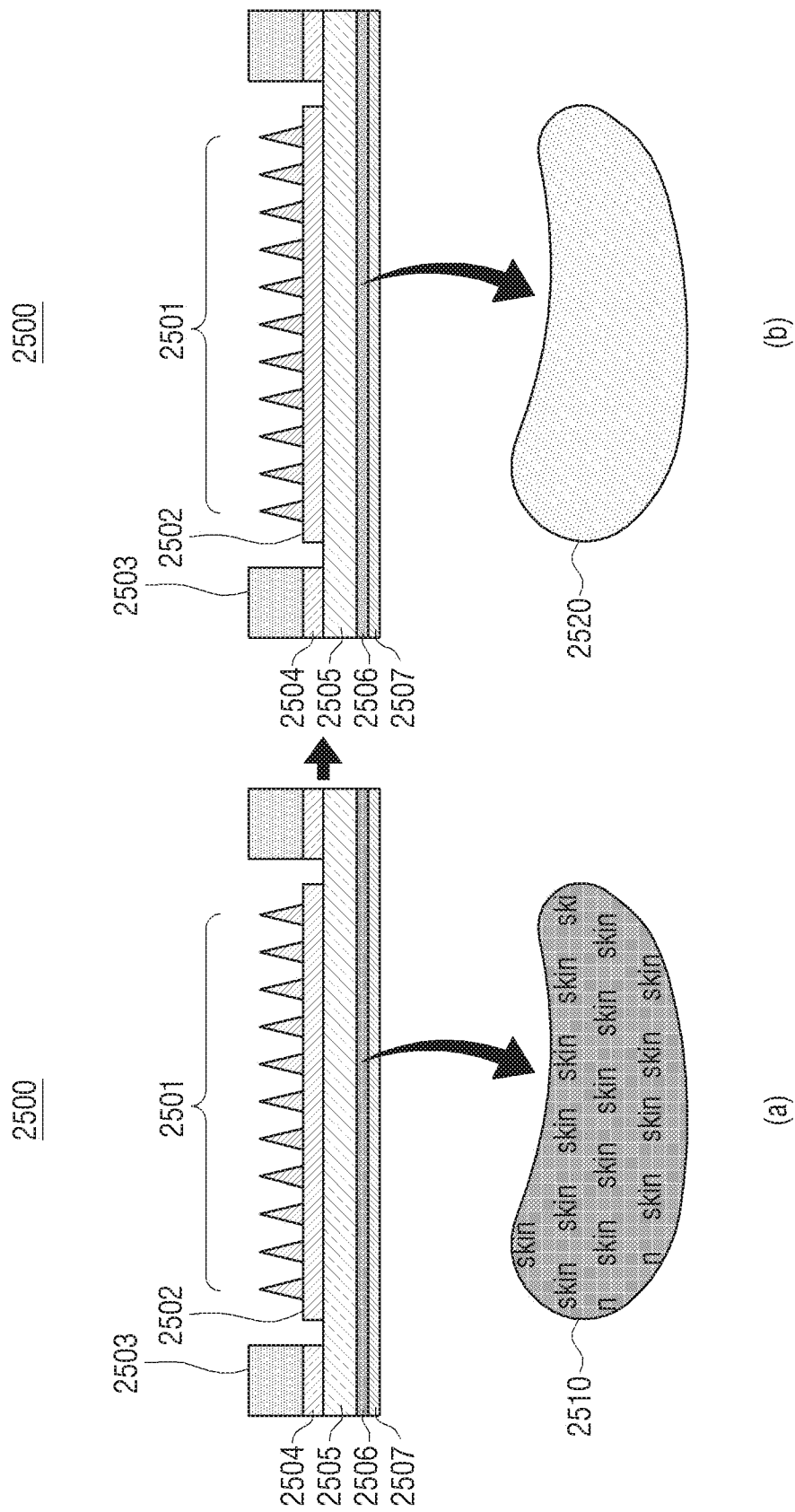
FIG. 25 is a cross-sectional view illustrating a patch according to an embodiment of the disclosure.

FIG. 25 is a cross-sectional view illustrating a patch according to an embodiment of the disclosure.

Referring to FIG. 25, a cross-section of a patch 2500 may include micro-needles 2501, a needle matrix 2502, a protective film 2503, an adhesive layer 2504, a patch matrix 2505, a discoloration layer 2506, and a release film 2507.

The micro needles 2501 may be formed of a biodegradable material or may store a bioactive material as described above.

The needle matrix 2502 may provide a surface in which the microneedles 2501 are arranged. The needle matrix 2502 may correspond to a needle sheet (or a base sheet) of FIG. 6.

The adhesive layer 2504 may be a layer adhered to the skin and include an adhesive material. The adhesive layer 2504 may correspond to a patch sheet (or, an adhesive sheet) of FIG. 6.

The protective film 2503 may support the micro-needles 2501 to keep in shape until the patch is adhered, and prevent the adhesive layer 2504 from being contaminated to maintain adhesion.

The protective film 2503 may be removed by a user when the patch is adhered.

The patch matrix 2505 may provide a surface in which the needle matrix 2502 and the adhesive layer 2504 are layered. The patch matrix 2505, the needle matrix 2502 and the adhesive layer 2504 may correspond to the support 601 of FIG. 6.

The discoloration layer 2506 may include a coloring material of which color changes depending on the temperature. The coloring material may include, for example, a thermochromic micro capsule.

The thermochromic micro capsule may be used mainly for visually identifying temperature changes with the naked eyes or used for functional fashion. The thermochromic micro capsule may be, for example, a functional dye that encapsulates one or more substances in a micro-sized microcapsule made of melamine or the like and reacts with each other according to an external conduction temperature. For example, at a temperature above a certain level, the first material may react with the first material in the capsule to exhibit the first color, and at a temperature below a certain range, the second material may react with the second material in the capsule to exhibit the second color.

The thermochromic micro capsule may be provided in the form of a slurry or a powder, which is a mixture of solid and liquid having fluidity, and may have various capsule thicknesses and sizes depending on the use.

Further, it is also possible to control the speed of the thermochromic micro capsule which changes according to the concentration depending on the temperature. For example, the higher the concentration of the thermochromic micro capsule, the faster the color change speed of the discoloration layer 2506 in accordance with the conduction of the temperature, and the lower the concentration of the thermochromic micro capsule, the slower the color change speed of the discoloration layer 2506 in accordance with the conduction of the temperature. That is, in consideration of the user's color change recognition, the color change speed of the discoloration layer 2506 may be appropriately adjusted according to the concentration of the coloring material.

2510 in FIG. 25 shows an example of the discoloration layer 2506. A variety of patterns, pictures (e.g., logos, etc.), texts, and the like may be printed on the discoloration layer 2506. In this case, the thermochromic micro capsule may be printed according to the patterns, printings, or texts for printing or printed on the discoloration layer 2506 except for the patterns, printings, or texts.

The release film 2507 may protect the discoloration layer 2506 and may be removed by the user when the patch is adhered as a film that maintains the overall shape of the patch. The release film 2507 may also include various patterns, shapes, pictures, logos or texts.

The patch 2500 described above may exhibit the first color, which is the color of the discoloration layer 2506, as in 2510 of FIG. 25 (a) before being adhered to the skin.

In this case, when the patch 2500 is closely adhered to the skin, the color of the ink corresponding to the first color may disappear in response to the temperature of the skin.

Then, as in 2520 of FIG. 25 (b), the patch may exhibit the second color. For example, if the first color is colored, the second color may have a colorless, transparent or skin-like color. If the second color is a transparent color, the skin color of the user may appear through the patch.

When the patch 2500 is not closely adhered to the skin, the first color may remain on the patch. A user who has confirmed that the first color has remained in the patch may regard the patch 2500 as not being closely adhered to the patch 2500 and try to closely adhere the patch 2500 to the skin.

Figure 26:
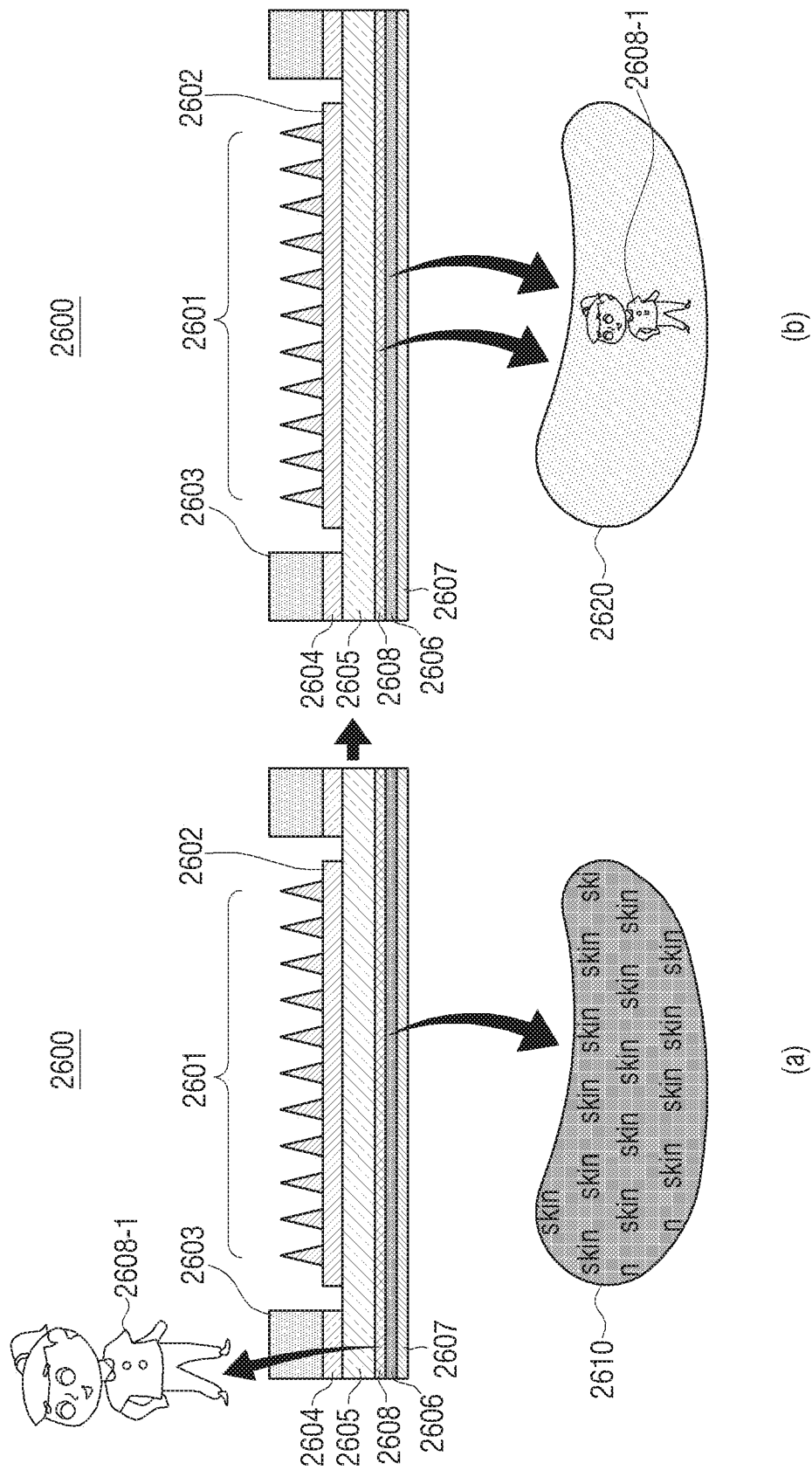
FIG. 26 is a cross-sectional view illustrating a patch according to another embodiment of the disclosure.

FIG. 26 is a cross-sectional view illustrating a patch according to another embodiment of the disclosure.

Micro needles 2601, a needle matrix 2602, a protective film 2603, an adhesive layer 2604, a patch matrix 2605, a discoloration layer 2606 and a release film 2607 of a patch 2600 in FIG. 26 respectively correspond to micro needles 2501, a needle matrix 2502, a protective film 2503, an adhesive layer 2504, a patch matrix 2505, a discoloration layer 2506 and a release film 2507 of a patch 2500 in FIG. 25. Therefore, the repeated description will be omitted.

Referring to FIG. 26, the patch 2600 may further include an image layer 2608. When the end portion of the micro needles 2610 faces downward, the image layer 2608 may be disposed under the discoloration layer 2606.

The image layer 2602 may have images such as various patterns, paintings (e.g., logos, characters (2608-1)) or texts printed thereon.

The patch 2600 may show the first color, which is the color of the discoloration layer 2606 as shown in 2610 of (a) of FIG. 26 before adhered to the skin.

When the patch 2600 is closely adhered to the skin, the ink color of the first color may disappear in response to the temperature of the skin.

Referring to 2620 of (b) of FIG. 26, the patch may show the second color. When the second color is a transparent color, the image 2608-1 printed on the image layer 2606 may be transparent through the discoloration layer 2606 that becomes transparent.

When the patch 2600 is firmly adhered to the skin and the image is thoroughly shown on the patch, a user may regard the patch 2600 to be closely adhered.

Figure 27:
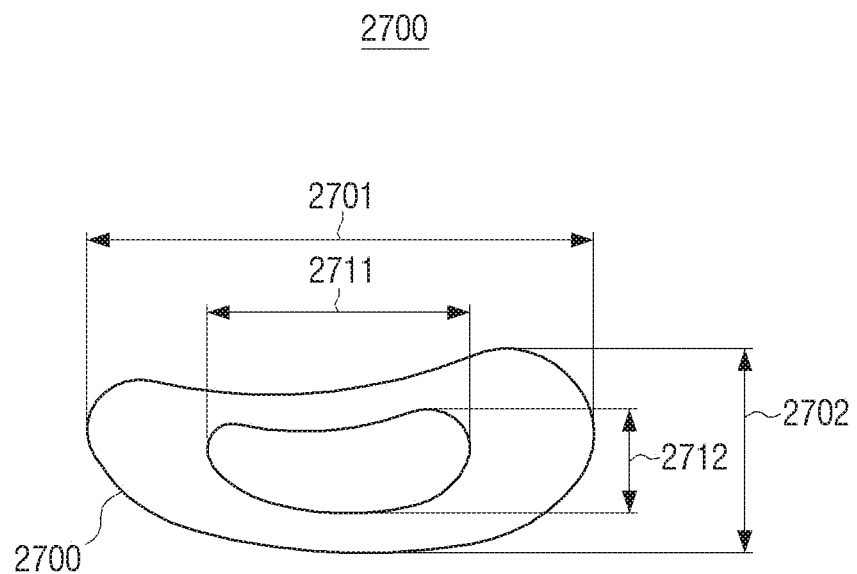
FIG. 27 is a view illustrating a shape of a patch according to an embodiment of the disclosure.

FIG. 27 is a view illustrating a shape of a patch according to an embodiment of the disclosure.

Referring to FIG. 27, a patch 2700 may include a needle area in which needles are arranged an adhesive area to be adhered to the skin.

In this case, at least part of the needle area may have adhesion.

The discoloration layer containing the thermochromic micro capsule may be disposed under at least one of the needle area and the adhesive area.

The discoloration layer may be disposed under a portion of the needle area or a portion of the adhesive area.

Referring to FIG. 27, a width 2701, which is the width of a patch 2700, may be a value between 30.0 mm and 80.0 mm, and a height 2702, which is the length of the patch 2700, may be a value between 10.0 mm and 30.0 mm. However, the disclosure is not limited to the above-described examples.

A width 2711 of the needle area, which is the width of a needle area, may be a value between 20.0 mm and 40.0 mm, and a height 2712, which is the length of the needle area, may be a value between 5.0 mm and 15.0 mm. However, the disclosure is not limited to the above-described examples.

Figure 28:
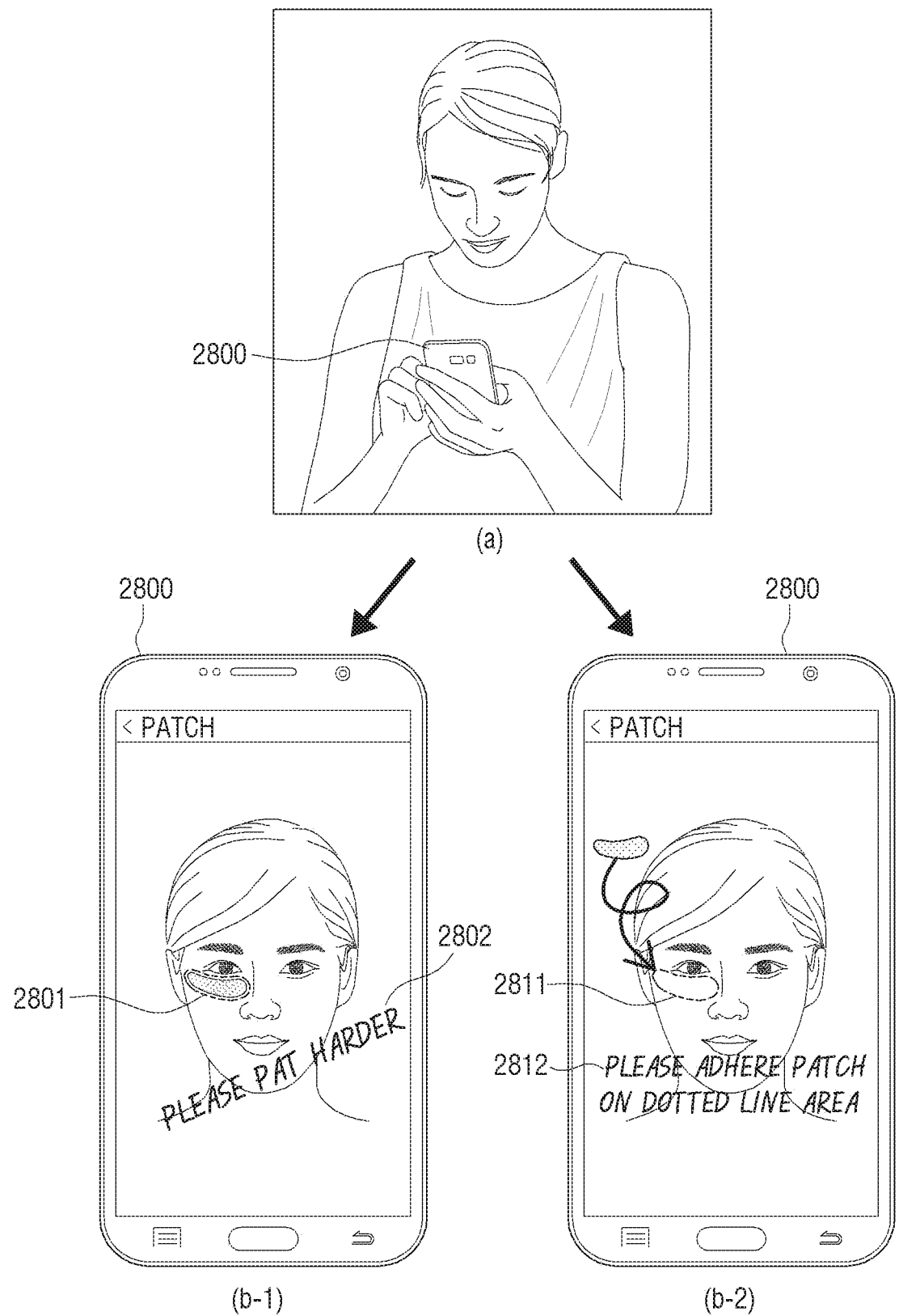
FIG. 28 is a view illustrating an electronic device for providing patch adherence information according to an embodiment of the disclosure.

FIG. 28 is a view illustrating an electronic device for providing patch adherence information according to an embodiment of the disclosure.

Referring to (a) of FIG. 28, a user may execute an application for skin care, and capture a face by using a camera provided in an electronic device 2800.

Referring to (b-1) of FIG. 28, patch adherence information based on adhesive state of the patch may be displayed on a screen of the electronic device 2800 together with the captured user's face.

For example, the electronic device 2800 may have information on the patch in advance. The patch information may include, for example, the use of the patch, the shape of the patch, the size of the patch, the adhesive position of the patch, the first color before the temperature sensing of the patch and the second color after the sensing of the patch, the image printed on the image layer of the patch, etc.

The electronic device 2800 may identify the adhesive state of the patch based on the patch information.

When a part of the patch indicates the first color before the temperature sensing because the patch is not firmly adhered to the skin, the electronic device 2800 may identify the adhesive state of the patch based on the area of the first color and the position of the first color. For example, when the area occupied by the first color relative to the total area of the patch is equal to or more than a certain ratio (e.g., 10% or more), the electronic device 2800 may identify that the patch is not firmly adhered to the skin.

When a part of the patch indicates the second color after the temperature sensing because the patch is not firmly adhered to the skin, the electronic device 2800 may identify the adhesive state of the patch based on the area of the second color and the position of the second color. For example, when the area occupied by the second color relative to the total area of the patch is equal to or less than a certain ratio (e.g., 90% or less), the electronic device 2800 may identify that the patch is not firmly adhered to the skin.

In addition, when only a certain ratio or less (e.g., 90% or less) of the entire image printed on the image layer of the patch is displayed because the patch is not closely adhered to the skin, the electronic device 2800 may identify that the patch is not firmly adhered to the skin.

An image recognition and process technology for a patch to recognize a color or an image is obvious to a person skilled in the art, and thus the detailed description will be omitted.

When it is identified that the patch is not firmly adhered to the skin, the electronic device 2800 may provide patch adherence information that prompts a user to adhere the patch firmly. The patch adherence information may include, for example, information 2801 indicating the patch not firmly adhered, or information requesting to adhere patch 2802 (e.g., please pat the patch harder)

Referring to (b-2) of FIG. 28, patch adherence information that guides the adhesive position of the patch may be displayed on the screen of the electronic device 2800.

For example, it is assumed that the user's skin condition is measured in advance, and the electronic device 2800 has the skin condition information. In this case, an device for measuring the skin condition may be the electronic device 2800 such as a portable terminal, or a skin measurement device, for example, an oil content meter, a moisture meter, a skin acidity meter, a skin fat meter, a skin texture meter, etc.

The electronic device 2800 may have the above-described patch information.

When a user captures a user's face, the electronic device 2800 may identify the area demanding the patch based on the user's skin condition information and the patch information.

Referring to (b-2) of FIG. 28, the electronic device 280 may provide patch adherence information indicating where the patch is adhered.

The patch adherence information may include, for example, information 2811 for highlighting the area where the patch is to be adhered and information requesting to adhere the patch to a proper position 2812 (e.g., "please adhere the patch to a dotted line area").

According to various embodiments, the patch adherence information can be naturally shown on the user's face with the augmented reality (AR) technique while the user photographs his or her face with the camera. The augmented reality technique may mean that a virtual image is combined with a real world viewed by a user and displayed as a single image. The augmented reality can also be referred to as a mixed reality (MR) because a virtual world including additional information in real time is combined into a real word to form a single image.

While a user rotates a face capturing the user's face with a camera, the patch adherence information providing the patch adhesive state or the patch adhesive position may be displayed on user's face in real time using an AR method.

FIG. 29 is a view illustrating an electronic device for providing patch adherence information according to another embodiment of the disclosure.

Referring to FIG. 29, a user may move her/his face while giving a gaze to a camera of an electronic device 2900.

The electronic device 2900 may generate patch adherence information in real time using a virtual reality method and provide the information to a screen.

For example, referring to (a) to (c) of FIG. 29, while the user rotates his/her face, the electronic device 2900 may provide patch adherence information on a screen.

The patch adherence information may include information 2901 and 2902 that highlights the adhesive area of the patch, and information 2911, 2912 and 2913 showing the patch adhesive state.

Referring to FIG. 29, it is impossible for a user to adhere or manage a patch while checking his/her face provided by using a virtual reality method in real time.

FIG. 30 is a flowchart to explain an electronic device to provide patch adherence information according to an embodiment of the disclosure.

Referring to FIG. 3001, an electronic device may acquire patch information.

As described above, the patch-related information may include information such as the purpose of the patch, the shape of the patch, the size of the patch, the adhesive area of the patch, the first color before the temperature sensing of the patch and the second color after the temperature sensing of the patch, the image printed on the image layer of the patch, etc.

The electronic device may acquire patch-related information from a server of a manufacturer that provides a patch. The electronic device may acquire patch information through a bar code or a QR code of a patch or a package of the patch.

Referring to operation 3003, the electronic device may acquire information on skin. The image information on skin may be image information on user' skin captured by a camera. In this case, operation 3001 may be performed prior to operation 3003.

Referring to operation 3005, the electronic device may generate patch adherence information based on the patch-related information and the image information on the skin.

The patch adherence information may provide information on the adhesive state of the patch or the adhesive positon of the patch as described above.

Referring to operation 3007, the electronic device may display the generated patch adherence information on a screen. For example, the electronic device may display the patch adherence information on a screen by using a virtual reality method.

A method of the disclosure according to an embodiment (e.g., operations) may be stored as commands stored in a computer readable non-transitory computer readable media in the form of a program module. When the command is executed by a processor, the processor may perform a function corresponding to the command.

The program may be stored in a computer-readable non-transitory recording medium, read and executed by a computer, thereby implementing an embodiment of the disclosure.

The non-transitory readable recording medium refers to a medium that semi-permanently stores data and is capable of being read by a device, but also includes a register, a cache, a buffer, etc., but does not include transmission media such as signal, current, etc.

Specifically, the above-described programs may be stored in a non-transitory readable recording medium such as a CD, a DVD, a hard disk, a Blu-ray disk, a USB, an internal memory, a memory card, a ROM, a RAM, etc.

The above-described programs may be stored in a memory of a server, transmitted to a terminal connected to a server via a network (e.g., an electronic device of the disclosure) for selling, or transferred or registered to a server by a provider of a program (e.g., a program developer or a program manufacturer).

When the programs are sold from a server to an electronic device, at least portion of the programs may be temporarily generated in a buffer of a server for transmission. In this case, a buffer of a server may be a non-transitory recording medium of the disclosure.

Also, when the above-described programs are sold to an electronic device via a relay server (for example, a relay server in an area where the electronic device is located), at least a part of the programs may be temporarily stored in the buffer of the relay server. In this case, the buffer of the relay server may be the non-transitory recording medium of the disclosure.

Additionally, the methods (e.g., operations) of the disclosure in accordance with an embodiment may be provided in a computer program product.

The computer program product may include the non-transitory recording medium described above. The computer program product may also be an application (or an app) itself that can be downloaded or uploaded to a server or other electronic device.

According to various embodiments, the subject of execution and the subject of storage of the computer program product may be the same or different. For example, when the storage subject of the computer program product is a server, the execution subject of the computer program product may be a terminal device.

According to various embodiments, there may be a system including a computer program product and an electronic device in which functions are performed by the computer program product. In this case, the electronic device can perform a function provided by the computer program product by control of a device in which the computer program product is installed.

According to an embodiment, a computer program product stores a program that causes an electronic device (or, a processor) to perform irradiating at least one light into skin to which a patch is adhered, detecting at least one reflective light based on the amount of moisture of the skin changed by physiologically active substances injected through the patch, generating patch adherence information indicating an adhesive state of a patch to the skin based on the detection result of at least one reflective light, and providing the generated patch adhesive state to an output unit or a communicator.

According to an embodiment, a computer program product stores a program that causes an electronic device (or a processor) to acquire patch related information and skin related image information, generate patch adherence information based on the patch related information and the skin related image information, and display the patch adherence information on a screen.

According to an embodiment, a computer program product stores a program for causing at least one electronic device (or a processor) to perform irradiating at least one light into the skin.

The above-description of the disclosure is intended to be illustrative, and it will be understood by those skilled in the art that various changes in form and details may be made therein without departing from the spirit and scope of the disclosure. It is therefore to be understood that the above-described embodiments are illustrative in all aspects and not restrictive. For example, each component described as a single entity may be distributed and implemented, and components described as being distributed may also be implemented in a combined form.

The scope of the disclosure is defined by the appended claims rather than the detailed description, and all changes or modifications derived from the meaning and scope of the claims and their equivalents are included in the scope of the disclosure.

What is claimed is:

1. A method for measuring skin condition using an electronic device, comprising:
   irradiating at least one light into skin to which a patch is adhered;
   detecting at least one reflective light based on an amount of moisture in the skin changed by physiologically active substances injected through the patch, in response to the at least one irradiated light;
   identifying a moisture level of the skin to which the patch is adhered based on a detection result;
   generating patch adherence information indicating an adhesive state of the patch to the skin based on the identified moisture level; and
   providing the generated patch adherence information to an output unit or a communicator of the electronic device,
   wherein the patch adherence information includes:
      information indicating that an entire area of the patch is adhered to the skin based on the identified moisture level being a value within a first range,
      information indicating a part of the patch is adhered to the skin based on the identified moisture level being a value within a second range, and
      information indicating that the patch is not adhered to the skin based on the identified moisture level being a value within a third range.

2. The method as claimed in claim 1, wherein the value within the first range, the value within the second range, and the value within the third range vary depending on the moisture level of the skin before the patch is adhered.

3. The method as claimed in claim 1,
   wherein the irradiating of the at least one light comprises irradiating a plurality of lights into the skin, and
   wherein the plurality of lights include a reference light with a smaller change in reflectivity with respect to a change in an object to be measured, and a measurement light with a greater change in reflectivity with respect to the change in the object to be measured.

4. The method as claimed in claim 3, wherein the detecting of the at least one reflective light comprises detecting a first reflective light corresponding to the reference light and a second reflective light corresponding to the measurement light.

5. The method as claimed in claim 4, wherein the detection result of the at least one reflective light includes an intensity of the first reflective light and an intensity of the second reflective light.

6. The method as claimed in claim 1, further comprising:
   setting at least one of an irradiation time, an irradiation intensity of the at least one irradiated light or a detection time of the at least one reflective light.

7. The method as claimed in claim 1,
   wherein the output unit includes a display, and
   wherein the method further comprises controlling the display to display visual information related to the patch adherence information on a screen.

8. An electronic device for measuring skin condition, comprising:
   an irradiation unit configured to irradiate at least one light into skin to which a patch is adhered;
   a detection unit configured to detect at least one reflective light based on an amount of moisture in the skin changed by physiologically active substances injected through the patch in response to the at least one irradiated light; and
   a controller configured to:
      identify a moisture level of the skin to which the patch is adhered based on a detection result of the at least one reflective light,
      generate patch adherence information indicating an adhesive state of the patch based on the identified moisture level, and
      provide the generated patch adherence information to an output unit or a communicator of the electronic device,
   wherein the patch adherence information includes:
      information indicating an entire area of the patch is adhered to the skin based on the identified moisture level being a value within a first range,
      information indicating a part of the patch is adhered to the skin based on the identified moisture level being a value within a second range, and
      information indicating the patch is not adhered to the skin based on the identified moisture level being a value within a third range.

9. The electronic device as claimed in claim 8, wherein the value within the first range, the value within the second range, and the value within the third range vary depending on the moisture level of the skin before the patch is adhered.

10. The electronic device as claimed in claim 8,
    wherein the irradiation unit irradiates a plurality of lights into the skin, and
    wherein the plurality of lights include a reference light with a smaller change in reflectivity with respect to a change in an object to be measured, and a measurement light with a greater change in reflectivity with respect to the change in the object to be measured.

* * * * *